(12) United States Patent
Palkar et al.

(10) Patent No.: US 11,285,167 B2
(45) Date of Patent: Mar. 29, 2022

(54) SYNERGISTIC NUTRITIONAL NEUROPROTECTIVE COMPOSITIONS FOR AMELIORATING NEURAL DYSFUNCTION

(71) Applicant: CELAGENEX RESEARCH (INDIA) PVT. LTD., Maharashtra (IN)

(72) Inventors: Jotiram Palkar, Thane (IN); Rajendra Prasad Tongra, Jaipur (IN)

(73) Assignee: CELAGENEX RESEARCH (INDIA) PVT. LTD., Thane (IN)

( * ) Notice: Subject to any disclaimer, the term of this patent is extended or adjusted under 35 U.S.C. 154(b) by 0 days.

(21) Appl. No.: 17/087,050

(22) Filed: Nov. 2, 2020

(65) Prior Publication Data
US 2021/0128593 A1    May 6, 2021

(30) Foreign Application Priority Data
Nov. 1, 2019   (IN) .............................. 201921044293

(51) Int. Cl.
| | |
|---|---|
| A61K 31/706 | (2006.01) |
| A23L 33/175 | (2016.01) |
| A23L 33/125 | (2016.01) |
| A23L 33/00 | (2016.01) |
| A61P 9/10 | (2006.01) |
| A61P 25/00 | (2006.01) |
| A61K 9/00 | (2006.01) |
| A61K 9/20 | (2006.01) |
| A61K 9/48 | (2006.01) |
| A61K 31/155 | (2006.01) |

(52) U.S. Cl.
CPC .......... *A61K 31/706* (2013.01); *A23L 33/125* (2016.08); *A23L 33/175* (2016.08); *A23L 33/40* (2016.08); *A61K 9/0053* (2013.01); *A61K 9/0095* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/485* (2013.01); *A61K 9/4858* (2013.01); *A61K 9/4866* (2013.01); *A61K 31/155* (2013.01); *A61P 9/10* (2018.01); *A61P 25/00* (2018.01); *A23V 2002/00* (2013.01)

(58) Field of Classification Search
CPC ... A61K 31/706; A23L 33/175; A23L 33/125; A61P 25/00
USPC .......................................................... 514/43
See application file for complete search history.

(56) References Cited

U.S. PATENT DOCUMENTS

| | | | | |
|---|---|---|---|---|
| 5,677,349 A | * | 10/1997 | Gilad | .................... A61K 31/155 |
| | | | | 514/634 |
| 2012/0164270 A1 | * | 6/2012 | Brenner | .................. C12P 19/28 |
| | | | | 426/15 |
| 2018/0071273 A1 | * | 3/2018 | Horn | ...................... A61K 36/87 |

OTHER PUBLICATIONS

OPTMZ; Jun. 25, 2019.*
Laube et al. (Biochemical Journal (2017) 474 2619-2640).*
Wang et al (Chinese Journal of Clinical Pharmacology and Therapeutics, vol. 23(9), 2018) (abstract sent).*
Conze et al. (Scientific Reports | (2019) 9:9772).*
Keynan et al. (Pain Medicine 2010; 11: 356-368).*
Kappelmann et al. (Molecular Psychiatry (2018) 23, 335-343).*

* cited by examiner

*Primary Examiner* — Shaojia A Jiang
*Assistant Examiner* — Michael C Henry
(74) *Attorney, Agent, or Firm* — Maschoff Brennan

(57) ABSTRACT

The present invention disclosed herein provides synergistic nutritional neuroprotective compositions for ameliorating neural dysfunction. Particularly, the invention relates to synergistic, efficient, nutritional composition for comprising specific combination of decarboxylated L-arginine called agmatine sulphate and nicotinamide riboside chloride, wherein agmatine sulphate and nicotinamide riboside chloride are present in the weight ratio of 1:0.05 to 1:2 along with pharmaceutically acceptable excipients. More particularly, the present invention offers synergistic effect for ameliorating neural dysfunction encompasses cerebrovascular diseases, neurodevelopmental disorders, mood disorders, mental health disorders and like thereof.

7 Claims, 12 Drawing Sheets

| | | | | |
|---|---|---|---|---|
| RA01 |  |  |  |  |
| RA02 |  |  |  |  |
| RA03 |  |  |  |  |
| RA04 |  |  |  |  |
| RA05 |  |  |  |  |
| RA06 |  |  |  |  |

| | | | | |
|---|---|---|---|---|
| RA01 |  |  |  |  |
| RA02 |  |  |  |  |
| RA03 |  |  |  |  |
| RA04 |  |  |  |  |
| RA05 |  |  |  |  |
| RA06 |  |  |  |  |

(a)

(b)

(c)

(d)

Male (a)  (b)

Female (c)  (d)

SYNERGISTIC NUTRITIONAL NEUROPROTECTIVE COMPOSITIONS FOR AMELIORATING NEURAL DYSFUNCTION

TECHNICAL FIELD OF THE INVENTION

The present invention relates to synergistic nutritional neuroprotective compositions for ameliorating neural dysfunction. Particularly, the invention relates to a synergistic, efficient, non-toxic, environmentally safe, therapeutically active, nutritional composition comprising a specific combination of an aminoguanidine compound and Sirtuin 1 activators and salts thereof along with pharmaceutically acceptable excipients or carriers. More particularly, the present invention relates to a nutrition composition having synergistic effect for ameliorating neural dysfunction which includes cerebrovascular diseases, neurodevelopmental disorders, mood disorders, mental health disorders and like thereof.

BACKGROUND AND PRIOR ART

Neuroprotection is defined as relative preservation of neuronal structure and/or function. It includes neuroprotective agents that provide protection against neuronal dysfunction, neuronal injury, neuronal death and neurodegeneration including degenerative processes such as inflammation, oxidative stress, immune dysfunction, and aggregation of related proteins or apoptosis.

Due to the stress associated with modern lifestyle, there is an extensive need for neuroprotection. Moreover, need of neuronal health in neurodevelopmental disorders, neuropsychiatric diseases, neurodegenerative disorders, and neurological disorder is highly urged.

Ischemia is generally caused by problems with blood vessels which leads to damage or dysfunction of tissue. Tissue injury or death occurs as a result of the initial ischemic insult, which is determined primarily by the magnitude and duration of the interruption in the blood supply, and then subsequent damage induced by reperfusion. During prolonged ischemia, ATP levels and intracellular pH decrease as a result of anaerobic metabolism and lactate accumulation. Ischemia results in tissue damage and sometimes cellular death by a process known as ischemic cascade.

Consequently, ATPase-dependent ion transport mechanisms become dysfunctional, contributing to increased intracellular and mitochondrial calcium levels (calcium overload), cell swelling and rupture, and cell death by necrotic, necroptotic, apoptotic, and autophagic mechanisms. Although oxygen levels are restored upon reperfusion, a surge in the generation of reactive oxygen species occurs and proinflammatory neutrophils infiltrate ischemic tissues to exacerbate ischemic injury. [*Int Rev Cell Mol Biol.* 2012; 298: 229-317].

Nitric oxide and its signaling pathway have an played important role in protection against ischemia/reperfusion injury. Enhancing the NO signaling pathway could become a widely accepted method for mimicking preconditioning effect, as this signaling plays an important role in both physiological and pathological conditions.

Nitric oxide (NO), synthesized from L-arginine by the enzyme nitric oxide synthase (NOS), seems to play an ambiguous role during tissue ischemia-reperfusion injury. Administration of nitric oxide (NO), NO donors or drugs that enhance NO realease (statins, calcium antagonists, ACE-inhibitors, dexamethasone) prior to ischemia protects the myocardium against ischemia/reperfusion injury.

Exogenous NO and endogenous NO may both play protective roles during ischemia and reperfusion injury. It is observed that, while exogenous administration of NO prior to ischemia can initiate a preconditioning-like phenomenon, endogenous NO-synthase (NOS)-derived NO is not involved in triggering or mediating the early phase of ischemic preconditioning's protection, but does play a pivotal role for initiating and mediating the delayed phase of ischemic preconditioning protection.

NO can preserve ischemic blood flow and attenuate platelet aggregation and neutrophil-endothelium interaction following ischemia/reperfusion. NO mediates protective as well as deleterious myocardial effects which are critically dependent on the specific experimental conditions [*Cardiovascular Research, Volume* 61, *Issue* 3, February 2004, Pages 402-413].

NO plays a dual role of neuroprotection and neurotoxicity during ischemia reperfusion. NO is mainly synthesized by three subtypes of NOS in brain tissue: nNOS, eNOS and iNOS. Endothelial NOS (eNOS) is also known as nitric oxide synthase 3 (NOS3) or constitutive NOS (cNOS), Neuronal NOS (nNOS) is also known as nitric oxide synthase 1 (NOS1) and Inducible NOS (iNOS) is also known as nitric oxide synthase 2 (NOS2) or calcium insensitive NOS. Among them, nNOS and eNOS are calcium-dependent NOS, and iNOS is calcium-independent. In general, nNOS and iNOS play a neuronal injury role in the early and late stages of ischemic stroke, while the activation of eNOS mainly exerts neuroprotection effects. NO is produced in different cells, such as endothelial cells, neurons, glial cells and neutrophils. It plays a dual role in different time and space in ischemic stroke. The beneficial or harmful role that NO plays in the brain tissue during an ischemic stroke depend on the cell type, the concentration of NO and microenvironment of ischemia [*Med Gas Res.* 2017 July-September; 7(3): 194-203].

NO production within endothelium may protect brain tissue, perhaps by hemodynamic mechanisms, whereas neuronal NO overproduction may lead to neurotoxicity [*J Cereb Blood Flow Metab.* 1996 September; 16(5):981-7].

Conversely, enhanced eNOS mediated nitric oxide release with intravascular eNOS substrate, L-arginine and nitric oxide donor drugs such as sodium nitroprusside result in smaller cerebral infarcts than those in vehicle (modified liposome) treated animals [*Trends Neurosci.* 1997 March; 20(3): 132-9].

The excitotoxic or ischemic conditions excessively activate nNOS, resulting in concentrations of NO that are toxic to surrounding neurons. Conversely, NO generated from eNOS is critical in maintaining cerebral blood flow and reducing infarct volume. iNOS, which is not normally present in healthy tissue, is induced shortly after ischemia and contributes to secondary late-phase damage [*Stroke.* 1997 June; 28(6):1283-8].

It appears that eNOS activation and subsequent NO release may act as a regulatory system to counterbalance the potentially deleterious effects of myocardial ischemia/reperfusion [*Nitric Oxide.* 2001 August; 5(4):317-33].

Sodium nitroprusside and nitroglycerin have been recently tested and proven effective in attenuating some of the injuries associated with ischemia and reperfusion [*J Invest Surg.* 2009 January-February; 22(1):46-55].

Among several known NO donor compounds, the ability of aminoguanidine to disrupt a major delayed neurodestructive pathway in ischaemia is an important difference from the neuroprotective therapies so far tried in humans. Advantageously, aminoguanidine is safe for human consumption [*J. Neurol Neurosurg Psychiatry* 1999; 67:1-3].

Aminoguanidine compounds are highly effective neuroprotective drugs as iNOS inhibitors and eNOS activators in ischemic condition.

In view of the above, the NOS pathway becomes essential for controlling ischemic injuries irrespective of the regions such as brain, heart, liver, limb etc, where all three isoforms of nitric oxide synthase enzyme activity need to be properly regulated.

It has been observed that, ischemic preconditioning triggers endogenous agmatine synthesis in the brain and liver, which reduces the brain infarct area and edema formation and attenuates ischemic injury effects by suppressing nNOS and iNOS expression. Agmatine, an endogenous neurotransmitter or neuromodulator, is an inhibitor of nitric oxide synthase [*Exp Neurobiol.* 2017 December; 26(6): 380-389]. Agmatine may have a pivotal role in endogenous ischemic tolerance. Therefore, the current inventors have selected agmatine as preferable aminoguanidine compound for experimental research and have found that agmatine not only suppresses nNOS and iNOS expression but also promotes overexpression of eNOS.

Silent information regulator 1 (SIRT 1) is a member of the sirtuin family of class III histone deacetylases. The class III histone deacetylases are distinguished from histone deacetylases in the other classes by their requirement of NAD for their enzyme activity.

Today, clinical treatment of cerebral ischemia, mostly stroke and cardiac arrest, is limited and new neuroprotective therapies are desperately needed. The Sirtuin family of oxidized nicotinamide adenine dinucleotide (NAD+)-dependent deacetylases has been shown to govern several processes within the central nervous system as well as to possess neuroprotective properties in a variety of pathological conditions such as Alzheimer's disease, Parkinson's disease, and Huntington's disease, among others.

SIRT1 deacetylates endothelial nitric oxide synthase (eNOS) to regulate vascular tone and maintain brain blood flow. SIRT1 dependent endothelial nitric oxide synthase (eNOS) modulation is another beneficial mechanism. Increased deacetylation of eNOS is suggested to increase NO production which regulates the vascular tone of blood vessels and helps maintain cerebral blood flow during chronic hypoperfusion [*Stroke.* 2014 November; 45(11): 3403-11].

It is also reported that pharmacological activation of SIRT1 due to resveratrol treatment 1 hour after an episode of MCAO (Middle cerebral artery occlusion), increased plasma NO and decreased infarction volumes in an eNOS dependent manner [*J Vasc Surg.* (2007)46:346-53].

Apart from eNOS modulation, the inventors have found the prominent role of SIRT1 activators in iNOS inhibition which is one of the highlights of the present invention and which imparts synergistic effect to the composition under ischemic conditions.

Major depressive disorder (MDD) also known simply as depression, is a mental disorder characterized by persistently depressed mood or loss of interest in activities, causing significant impairment in daily life. Low self-esteem, loss of interest in normally enjoyable activities, low energy, and pain without a clear cause are common symptoms. The World Health Organization estimates that more than 300 million individuals are affected by MDD at present, and the number of individuals affected by this disorder increased by almost 20% in the last 10 years. MDD is now the leading cause of disability worldwide. It is estimated that up to 50% of the 800,000 suicides that occur per year worldwide are associated with MDD, and patients affected by this disorder are almost 20-fold more likely to die by suicide than the general population. Therefore, appropriate and effective treatments are necessary to be established for a better management of this disorder. The most promising therapeutic strategy for this challenge emerged at the beginning of the 21st century, when Berman et al. demonstrated for the first time that the N-methyl-D-aspartate (NMDA) receptor antagonist ketamine caused fast and long-lasting antidepressant effects. Despite the promising effects of ketamine, its prolonged use has some limitations, mainly related to side effects and the possibility of neurotoxic effects upon chronic use.

Considering the limitation of widespread clinical use of ketamine, the search of compounds that might share similar mechanisms of action to ketamine emerges as a promising therapeutic strategy. Regarding this issue, the present inventors have focused on the investigation of the possible role of endogenous glutamatergic neuromodulators for fast antidepressant responses, where they found that agmatine played a significant role in antidepressant activity.

Notably, increased agmatine concentrations are evident in the serum of MDD patients and reduced concentrations of agmatine were shown in the cerebral cortex of suicides, suggesting a role of this neuromodulator in the pathophysiology of MDD.

Neurodevelopmental disorders are impairments of brain growth and development affecting several brain functions, and include cognitive, motor, language, learning, and behavioural disorders due to many causes such as genetic, lesional, and environmental.

Developmental disorders like autism differ from mental illness in several important ways. Developmental disorders generally appear at birth or during childhood and are diagnosed by the age of 18. Unlike mental illness, which can be successfully treated, developmental disorders are lifelong disabilities.

While mental illness and developmental disorders have key differences, they also have some similarities. Both are diagnosed and treated by mental health professionals, including therapists, psychologists, and psychiatrists, and both are found in the Diagnostic and Statistical Manual of Mental Disorders, which is used to diagnose mental conditions. Both mental illness and autism occur in people of all ethnic, racial and economic groups. However, it is around four times more common among boys than among girls, according to the Centers for Disease Control and Prevention [USA].

In general, mental illness is believed to be caused by a range of factors, including genetic traits, environmental exposures, brain chemistry, and environmental factors.

Autistic disorder typically involves language delays, communication challenges, social problems, and unusual interests and behaviors.

Asperger syndrome involves milder symptoms than autistic disorder and doesn't usually include language or intellectual delays or disabilities.

Researchers yet do not know the exact causes of autism spectrum disorder [ASD], but studies suggest that both genetic and environmental factors come into play. Some of the risk factors for ASD include: having a sibling with autism, having older parents, having very low birth weight, having certain genetic conditions such as Down syndrome, Rett syndrome and signs and symptoms of ASD.

In ASD, aerobic glycolysis, called Warburg effect, gets stimulated through activation of glucose transporter (Glut), pyruvate kinase M2 (PKM2), pyruvate dehydrogenase kinase 1 (PDK1), monocarboxylate lactate transporter 1 (MCT-1), lactate dehydrogenase kinase-A (LDH-A) and inactivation of pyruvate dehydrogenase complex (PDH). The aerobic glycolysis converts glucose into lactate regardless of oxygen. Aerobic glycolysis is less efficient in terms of ATP production than oxidative phosphorylation because of the shunt of the TCA (tricarboxylic acid) cycle.

Dysregulation of energetic metabolism might promote cell deregulation and progression of ASD. Warburg effect regulation could be an attractive target for developing therapeutic interventions in ASD.

Mammalian target of rapamycin (mTOR) is a key regulator in various cellular processes, including cell growth, gene expression, and synaptic functions. Autism spectrum disorder (ASD) is frequently accompanied by monogenic disorders, such as tuberous sclerosis complex, phosphatase and tensin homolog tumor hamartoma syndrome, neurofibromatosis 1, and fragile X syndrome, in which mTOR is hyperactive. Evidences indicate a pathogenic role for hyperactive mTOR-mediated signaling in ASD associated with these monogenic disorders, and mTOR inhibitors are a potential pharmacotherapy for ASD [*CNS Neurol Disord Drug Targets*. 2016 June; 15(5): 533-543].

It has previously been observed that resveratrol, prevents valproic acid-induced social impairment in these animals. Furthermore, ketogenic diets have been shown to be somewhat effective in controlling ASD behavioural symptoms in human subjects [*Neurol Disord Therap*, 2018, 2(2): 1-5].

The inventors of the invention have surprisingly found that agmatine is a potent and essentially non-toxic endogenous molecule which can decrease glycolysis, possibly via effects on mTOR. It further inhibits protein glycation and thereby ameliorates some of the consequences of increased glycolytic activity and exerts beneficial effects on aspects of behaviour in ASD children.

Several studies have investigated mTOR signaling in developmental and neuronal processes and have found that, when dysregulated, it could contribute to the development of ASD. Although many potential mechanisms still remain to be fully understood, these associations are of great interest because of the clinical availability of mTOR inhibitors. Clinical trials evaluating the efficacy of mTOR inhibitors to improve neurodevelopmental outcomes have been initiated. The role of mTOR signaling in different brain regions and its upstream and downstream targets may provide novel insights into the development of therapeutic approaches for the management of developmental disorders [*Journal of Receptor, Ligand and Channel Research* 2015:8 65-74].

The inventors have observed that in many neurological, mental and neurodevelopmental disorders, depletion of NAD$^+$ levels, increase in oxidative stress, neuroinflammation, ROS formation, defects in synaptic proteins, disruption of E-I (excitation and inhibition) balance are common factors that need to be resolved.

Serendipitously, the inventors found that the synergistic combination of neuromodulators along with NAD$^+$ boosting molecules (NBMs) or sirtuin-activating compounds afford fantastic results in neuroprotection by improving or ameliorating different pathways like NOS, NMADR and mTOR.

Objective of the Invention

The primary objective of the invention is to provide a synergistic nutritional composition for managing neuronal health.

A further objective of the invention is to provide a therapeutically active, nutrient based, non-toxic, safe, neuroprotective composition.

Yet another objective of the invention is to provide a synergistic nutritional combination of a neuromodulator and a sirtuin activator for treating cerebrovascular ischemia, neurodevelopmental disorders, mood disorders, mental health disorders and the like thereof.

A further objective of the invention is to develop a nutrient based composition that improves developmental disability and mood instability.

Another objective of the invention is to provide a combination of therapeutically active nutrients that work synergistically by modulating NOS signaling pathway.

A further objective of the invention is to provide a nutritional combination that works synergistically by regulating NMDAR signaling pathway.

Another objective of the invention is to provide a nutritional combination that works synergistically by ameliorating mTOR signaling pathway.

Another objective of the invention is to provide a therapeutically effective, safe, nutrient based remedy for site specific action with no adverse effects.

SUMMARY OF THE INVENTION

To meet the above objectives, the inventors of the present invention carried out thorough experiments to establish therapeutic effects of the bioactive ingredients or nutrients or nucleoside or substances present in the composition that protect against ischemia induced cell death/damage in a subject in need thereof.

In a particular aspect, the invention relates to synergistic nutritional compositions comprising therapeutically active nutrients along with pharmaceutically acceptable carriers for improving brain health.

In another aspect, the invention provides an advanced neuroprotective combination therapy which comprises a synergistic combination of an aminoguanidine compound and SIRT1 activators along with pharmaceutically acceptable carriers.

In another particular aspect, the present invention provides potent synergistic nutritional neuroprotective compositions for treating cerebrovascular ischemia, neurodevelopmental disorders, mood disorders, mental health disorders and like thereof comprising a specific combination of an aminoguanidine compound and SIRT1 activators present in suitable weight ratio along with pharmaceutically acceptable carriers.

In another aspect, the present invention offers synergistic nutritional neuroprotective compositions, wherein the aminoguanidine compound is decarboxylated L-arginine also called agmatine (AGM) and SIRT1 activators are selected from the group consisting of nicotinamide riboside (NR), nicotinic acid (NA), nicotinamide (NAM), nicotinamide mononucleotide (NMN), N(1)-methyl nicotinamide (1-MNA) and salts thereof.

More particularly, the present invention provides a nutritional neuroprotective remedy comprising a synergistic combination of agmatine sulphate and nicotinamide riboside chloride, which are present in therapeutically effective amounts, along with pharmaceutically acceptable carriers.

In a further aspect, the present invention provides a synergistic nutritional composition, wherein the bioactive moieties present in therapeutically effective amount synergistically provide protection from circuit disorder or neuronal and synaptic dysfunction.

In another aspect, the invention provides a synergistic effect, wherein agmatine sulphate increases expression of eNOS and inhibits nNOS that improves blood flow through vasodilation; while iNOS protein expression is concomitantly decreased by nicotinamide riboside chloride that controls vascular/cellular inflammation.

In another aspect, the invention provides a synergistic effect wherein, agmatine sulphate inhibits NMDAR activity and nicotinamide riboside chloride concomitantly augments neurogenesis.

In another aspect, the invention provides a synergistic effect wherein, agmatine sulphate inhibits over expression of mTOR activity and nicotinamide riboside chloride concomitantly improves neural and synaptic plasticity.

In another aspect, the invention provides a cost effective, non-toxic, efficient, and environmentally safe neuroprotective composition comprising a synergistic combination of nutrients without any adverse effect.

In yet another aspect, the invention relates to synergistic nutritional compositions comprising a combination of agmatine sulphate and salts thereof present in a range of 1-3000 mg and sirtuin 1 activator(s) and salts thereof present in a range of 1-1000 mg; along with pharmaceutically acceptable excipients/carriers, and optionally in presence of bioenhancer.

Abbreviations

AGM: Agmatine
NOS: Nitric oxide synthase
eNOS: Endothelial nitric oxide synthase
iNOS: inducible nitric oxide synthase
nNOS: Neuronal nitric oxide synthase
NR: Nicotinamide riboside
SIRT1: Sirtuin (silent mating type information regulation 2 homolog) 1
TNF-alpha: Tumour Necrosis Factor alpha
IL-6: Interleukin 6
mTOR: mammalian target of rapamycin
NMDAR: N-methyl-D-aspartate receptor
MDD: Major depressive disorder
ASD: Autism spectrum disorder
TTC: Tetrazolium chloride staining
LDH: Lactic acid dehydrogenase
OXT: Oxytocin
VPA: Valproic acid
PND: Postnatal day

DETAILED DESCRIPTION OF THE INVENTION

Figure 1:
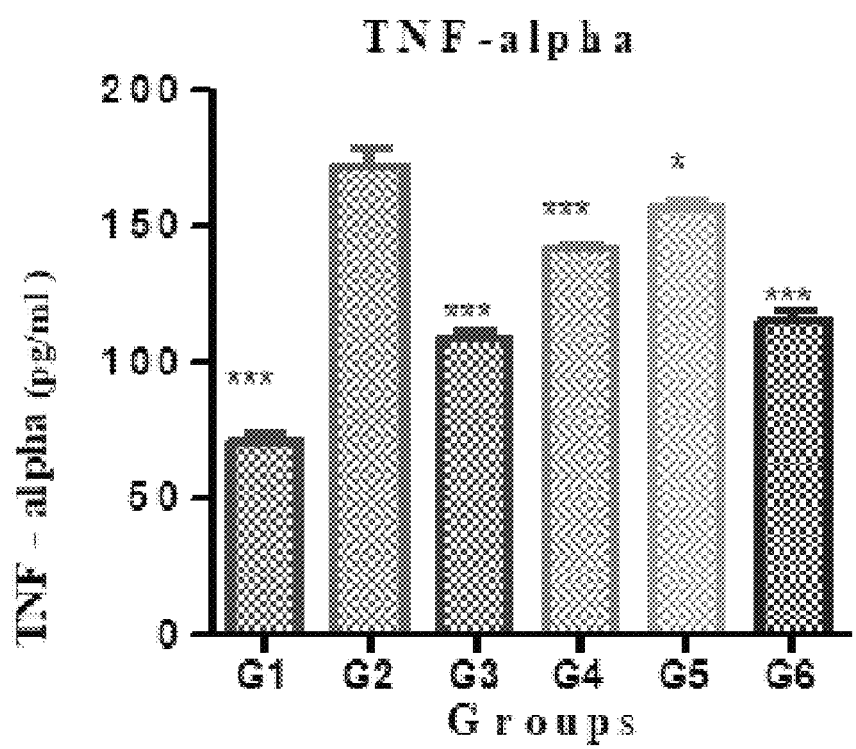
FIG. 1 illustrates the effect of test substances on Rat TNF alpha levels

The invention will now be described in detail in connection with certain preferred and optional embodiments, so that various aspects thereof may be more fully interpreted and comprehended. However, any skilled person in the art or artisan will appreciate the extent to which such embodiments could be generalized in practice.

It is further to be understood that all terminology used herein is for the purpose of describing particular embodiments only and is not intended to be limiting in any manner or scope.

Unless defined otherwise, all technical and scientific expressions used herein have the same meaning as commonly understood by one of ordinary skill in the art to which embodiments of the invention pertain.

In describing and claiming the embodiments of the present invention, the following terminology will be used in accordance with the definitions set out below which are known in the art.

The singular forms "a," "an," and "the" include plural reference unless the context clearly dictates otherwise. Also, the term 'composition' does not limit the scope of the invention and it may include multiple compositions to establish best mode of the invention.

The term "pharmaceutically/nutraceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Particularly, the term "pharmaceutically-acceptable salts" refers to the relatively non-toxic, inorganic and organic acid addition salts of compounds, alkali or alkaline earth metal salts, as well as solvates, co-crystals, polymorphs, isomers, enantiomers, congeners, hydrates and like thereof.

In an additional embodiment, the present composition may comprise a bioenhancer that improves the in-vivo bioavailability by ameliorating solubility and absorption of the composition.

Certain compounds of the present invention exist in unsolvated forms as well as solvated forms, including hydrated forms. Further, some compounds of the present invention exist in multiple crystalline or amorphous forms ("polymorphs"). In general, all physical forms are of use in the methods contemplated by the present invention and are intended to be within the scope of the invention. Compound or pharmaceutically acceptable salts, hydrates, polymorphs or solvates of a compound intend the inclusive meaning of "or", in that materials meeting more than one of the stated criteria are included, e.g., a material that is both a salt and a solvate is encompassed. Compounds of the invention exist in particular geometric, enantiomeric, stereoisomeric or diastereomeric forms. The invention contemplates all such compounds, including dextrorotatory and levorotatory-isomers, rectus and sinister configuration. All such isomers, as well as racemic mixtures thereof, are intended to be included in this invention.

As used herein, the term "comprising" is intended to mean that the compositions, methods, indications include the recited elements, but does not exclude others.

In a preferred embodiment, the invention provides a nutritional, synergistic, neuroprotective composition comprising a combination of an effective amount of an aminoguanidine compound and SIRT1 activators along with pharmaceutically acceptable carriers.

In another embodiment, the invention provides a non-toxic, cost effective and efficient nutrient based medicament for treating cerebrovascular ischemia, neurodevelopmental disorders, mood disorders, mental health disorders and like thereof.

In another particular embodiment, the invention provides a synergistic nutritional composition, wherein one active moiety is an aminoguanidine compound or its acceptable salts such as bicarbonate, hydrochloride, sulphate, nitrate, orotate and likewise.

Particularly, the aminoguanidine compound is an agmatine salt. In a preferred embodiment, the aminoguanidine compound is agmatine sulphate.

Agmatine is an amine, synthesized by decarboxylation of L-arginine by arginine decarboxylase (ADC). Moreover, it is a natural metabolite of the amino acid arginine and conjugate base of an agmatinium. It is found naturally in ragweed pollen, ergot fungi, octopus muscle, herring sperm, sponges, and the mammalian brain.

In another embodiment, the invention provides synergistic nutritional compositions comprising Agmatine and salts thereof, wherein the preferable salt is sulphate. Agmatine sulphate having the molecular formula $C_5H_{16}N_4O_4S$ is represented by Formula I below.

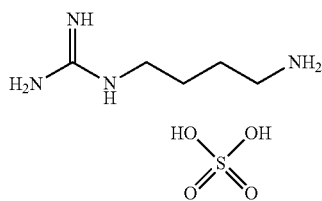

(I)

Agmatine is the decarboxylated form of L-Arginine and is chemically known as 1-Amino-4-guanidinobutane, 4-(Aminobutyl) guanidine or N-4-Aminobutylguanidine.

Agmatine is an amine formed by the enzymatic decarboxylation of L-arginine by arginine decarboxylase. Agmatine meets most of the criteria for it to be established as a potent neurotransmitter/neuromodulator in the CNS.

In another embodiment, the invention provides a nutritional, naturally resourced composition, wherein AGM induces eNOS activation and inhibits nNOS overexpression through NO signaling pathway.

It is noteworthy that, agmatine favors eNOS activation and enhances nitric oxide (NO) in the muscles slightly. An increase in NO in the muscles is linked with greater blood flow (also known as vasodilation), and thus, a better "pump." A better pump does two things. First, it increases nutrient delivery to the working cells, and second, it accelerates protein synthesis, so it improves cellular growth.

In another embodiment, the invention provides a synergistic nutritional composition comprising therapeutically effective amount of AGM or salts thereof, wherein AGM sulphate is present in a range of 1-3000 mg of the total composition. Particularly, AGM sulphate is present in a range of 1-1000 mg of the total composition.

In another preferred embodiment, the invention provides a synergistic nutritional composition, wherein the other active moiety is SIRT1 activator(s).

Sirtuin 1, also known as NAD-dependent deacetylase sirtuin-1, is a protein that in humans is encoded by the SIRT1 gene. SIRT1 (mammalian) is a member of the sirtuin family. SIRT1 stands for sirtuin (silent mating type information regulation 2 homolog) 1.

In yet another embodiment, the SIRT1 activators are particularly NAD precursors which are selected from the group consisting of nicotinamide riboside (NR), nicotinic acid (NA), nicotinamide (NAM), and/or nicotinamide derivatives such as nicotinamide mononucleotide (NMN), N(1)-methyl nicotinamide (MNA) and pharmaceutically acceptable salts thereof. In another preferred embodiment, the SIRT1 activator is nicotinamide riboside chloride. It has the chemical formula $C_{11}G_{15}ClN_2O_5$ and is represented by Formula II below.

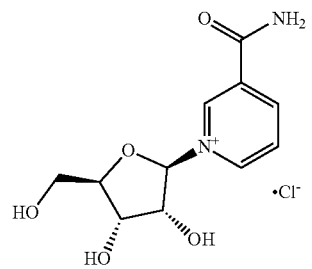

Formula II

During ischemic condition or injury, iNOS expression gets unregulated which is responsible for NF-kB activation that eventually targets inflammation by increasing the production of inflammatory cytokines, chemokines, and adhesion molecules.

Nicotinamide riboside chloride is used as SIRT1 activator in the composition to manage synergistic effect that deacetylates NF-κB and subsequently inhibits iNOS expression. This inhibition regulates ROS production and attenuates inflammation.

In a further embodiment, the invention provides a synergistic nutritional neuroprotective composition comprising a therapeutically effective amount of SIRT1 activator along with pharmaceutically acceptable salts thereof, wherein the SIRT1 activator, preferably nicotinamide riboside chloride is present in a range of 1-1000 mg of the total composition.

In another embodiment, the present composition optionally comprises a bioenhancer that improves the in-vivo bioavailability by ameliorating solubility and absorption of the composition.

Glutamate-induced neuronal damage is mainly caused by overactivation of N-methyl-D-aspartate (NMDA) receptors. Conversely, normal physiological brain function and neuronal survival require adequate activation of NMDA receptors.

In another embodiment, the invention provides a synergistic nutritional neuroprotective composition, wherein agmatine sulphate enhances the antidepressant potency of the NMDA receptor antagonist.

In the present invention, the composition exhibits neuroprotective properties and provides protection against neurotoxicity induced by excitotoxins or higher concentrations of glucocorticoids in patients with major depression. It further reduces astrocyte hypertrophy and microglia activation. Thus, the composition improves mood function and plays an antidepressant effect.

In a further embodiment, the present synergistic nutritional neuroprotective composition enhances hippocampal neurogenesis and prevents aging-associated memory loss and mood dysfunction. In the same way, the antidepressant effect of the composition is associated with hippocampal BDNF activation in a subject with depression disorder.

In another embodiment, the invention provides a synergistic nutritional neuroprotective composition, wherein the synergistic combination of AGM and SIRT1 activators reduces lactate production in autistic spectrum disorders (ASD) patients by inhibiting overexpression of mTOR.

In another embodiment, the invention provides a synergistic nutritional neuroprotective composition, wherein the active moieties influence cellular energy metabolism, via effects on mTOR, thereby decreasing glycolysis, enhancing mitochondrial activity, and thus countering the onset of Warburg-like metabolism.

Autism spectrum disorders (ASD) is accompanied, associated and/or related to changes in energy metabolism, more specifically the imposition of enhanced aerobic glycolysis, coupled with a suppression of mitochondrial ATP synthesis.

In another embodiment, the present synergistic composition efficiently enhances mitochondrial ATP production and reduces the elevated levels of inflammatory cytokines such as tumor necrosis factor TNF alpha, interferon-$\alpha$, IL1$\alpha$, Interleukin-6, IL8, IL12, and lactate dehydrogenase in the blood mononuclear cells, serum, plasma, and cerebrospinal fluid of autistic subjects.

Moreover, the present synergistic nutritional composition improves oxidative stress, mitochondrial dysfunction, and altered tryptophan metabolism in ASD.

More particularly, the present invention offers synergistic neuroprotective effects of combined agmatine sulphate and nicotinamide riboside chloride for treating cerebral ischemia, MDD and ASD. The composition imparts significant neuroprotective effect on the subject in need thereof along with enhanced bioavailability and efficacy.

In one preferred embodiment, the invention provides a synergistic nutritional neuroprotective composition(s) for a subject in need thereof comprising a therapeutically active exogenous combination of a crystalline form of decarboxylated L-arginine and sirtuin 1 activators and salts thereof, wherein the crystalline form of the decarboxylated L-arginine and sirtuin 1 activators are present in a weight ratio of 1:0.05 to 1:2 along with pharmaceutically acceptable excipients.

In a preferred embodiment, the invention provides a potent synergistic nutritional composition for ameliorating neural dysfunction in a subject in need thereof comprising a therapeutically active exogenous combination of crystalline agmatine sulphate and a sirtuin 1 activator and salts thereof, wherein the crystalline agmatine sulphate and sirtuin 1 activator are present in a weight ratio of 1:0.05 to 1:2 along with pharmaceutically acceptable excipients.

In another preferred embodiment, the invention provides potent synergistic nutritional compositions for ameliorating neural dysfunction comprising a therapeutically active exogenous combination of crystalline form of agmatine and nicotinamide riboside and salts thereof, present in a weight ratio of 1:0.05 to 1:2 along with pharmaceutically acceptable excipients.

In another preferred embodiment, the invention provides a synergistic neuroprotective nutritional composition for ameliorating developmental disorders comprising a therapeutically active exogenous combination of agmatine sulphate and nicotinamide riboside chloride thereof, present in a weight ratio of 1:0.05 to 1:2 along with pharmaceutically acceptable excipients.

In another preferred embodiment, the invention provides synergistic nutritional compositions for stabilizing mental disorder or mood disorder comprising a therapeutically active exogenous combination of agmatine sulphate and nicotinamide riboside chloride present in a weight ratio of 1:0.05 to 1:2 along with pharmaceutically acceptable excipients.

In another preferred embodiment, the invention provides synergistic nutritional compositions for treating ischemic brain damage comprising a therapeutically active exogenous combination of agmatine sulphate and nicotinamide riboside chloride present in a weight ratio of 1:0.05 to 1:2 along with pharmaceutically acceptable excipients.

In yet another embodiment, the invention provides a synergistic combination, wherein the decarboxylated L-arginine salt is agmatine sulphate which is present in crystalline form with organoleptic properties (such as smell, taste, colour, texture).

The term 'organoleptic' pertains to the analysis of the properties of products and materials (mainly foodstuffs) by means of the sense organs. Organoleptic testing is usually done by tasters. It is the property of the substances that create an individual experience via the senses including taste, sight, smell, and touch.

In yet another preferred embodiment, the invention discloses a synergistic nutritional neuroprotective composition comprising a therapeutically active exogenous blend of crystalline form of organoleptic agmatine sulphate and nicotinamide riboside chloride, wherein organoleptic agmatine sulphate and nicotinamide riboside chloride are present in a weight ratio of 1:0.05 to 1:2. In a preferred embodiment, the organoleptic agmatine sulphate and the nicotinamide riboside chloride are present in a weight ratio of 1:0.1 to 1:1 along with pharmaceutically acceptable excipients.

In one more embodiment, the invention provides a synergistic nutritional composition comprising a crystalline form of decarboxylated L-arginine present in a range of 50% to 90% by weight of the total composition.

In a further embodiment, the invention provides an anti-ischemic synergistic nutritional composition comprising white crystalline agmatine sulphate present in a range of 50% to 90% by weight of the total composition.

In yet another embodiment, the invention provides a synergistic nutritional composition comprising a sirtuin 1 activator present in a range of 10% to 50% by weight of the total composition.

In yet another embodiment, the invention provides a synergistic nutritional composition comprising white crystalline nicotinamide riboside chloride present in a range of 10% to 50% by weight of the total composition.

In another embodiment, the invention provides a method for ameliorating brain function in a subject in need thereof comprising, oral administration of a therapeutically effective amount of a nutritional neuroprotective composition comprising an exogenous synergistic blend of agmatine and sirtuin 1 activators and salts thereof present in a weight ratio of 1:0.05 to 1:2, along with pharmaceutically acceptable excipients.

In another embodiment, the invention provides a method for ameliorating brain function in a subject in need thereof comprising, oral administration of a therapeutically effective amount of a nutritional neuroprotective composition comprising a synergistic combination of white crystalline agmatine sulphate and sirtuin 1 activators with pharmaceutically acceptable excipients, wherein the white crystalline agmatine sulphate is present in a range of 50% to 90% and the sirtuin 1 activator is present in a range of 10% to 50% by weight of the total composition.

In another embodiment, the invention provides a method of reducing likelihood of depression symptoms in a subject comprising, administering to the patient an effective amount of a nutritional composition comprising a therapeutic combination of agmatine and sirtuin 1 activators and salts thereof present in a weight ratio of 1:0.05 to 1:2, along with pharmaceutically acceptable excipients.

In yet another embodiment, the invention provides a method of improving autism disorder symptoms in a subject comprising, administering to the patient an effective amount of a nutritional composition comprising a therapeutic combination of agmatine and sirtuin 1 activators and salts thereof present in a weight ratio of 1:0.05 to 1:2, along with pharmaceutically acceptable excipients.

In yet another embodiment, the invention provides, a method of treating cerebral ischemia or stroke in a subject comprising, administering to the patient an effective amount of nutritional composition comprising a therapeutic combination of agmatine and sirtuin 1 activators and salts thereof present in a weight ratio of 1:0.05 to 1:2, along with pharmaceutically acceptable excipients.

In another embodiment, the invention provides a method for ameliorating neural dysfunction, wherein agmatine sulphate is present in a range of 45% to 90% and sirtuin 1 activator is present in a range of 10% to 45% by weight of the total composition.

In another embodiment, the invention provides a potent synergistic neuroprotective composition comprising a therapeutically active nutritional combination of crystalline agmatine sulphate and nicotinamide riboside chloride present in a weight ratio of 1:0.05 to 1:2 along with pharmaceutically acceptable excipients.

In another embodiment, invention provides a potent synergistic neuroprotective composition comprising a therapeutically active nutritional combination of crystalline agmatine sulphate and nicotinamide riboside chloride, wherein agmatine sulphate is present in a range of 40% to 90% and nicotinamide riboside chloride is present in a range of 10% to 40% by weight of the total composition.

In the present invention, the term 'hybrid neuroprotective therapy' or 'combination therapy' or 'concomitant therapy' denotes the characteristics or inventive feature of the present composition, wherein the two active moieties performing simultaneous functions in systematic pathways without any deviation or overlapping of the mechanism, consequently, improve brain function.

In an additional embodiment, the invention provides an additional bioenhancer to improve the bioavailability of the present composition by enhancing the absorption of active ingredients inside the body.

As used herein, the term "therapeutically effective amount" is intended to mean the amount of active compounds of the present invention to be effective for treating cerebral ischemia induced diseases or conditions through synergistic effect.

The term 'Neurodevelopmental disorders' define disabilities in the functioning of the brain that affect a child's behaviour, memory or ability to learn e.g. mental retardation, dyslexia, attention deficit hyperactivity disorder (ADHD), learning deficits and autism.

In yet another embodiment, the invention provides a synergistic nutritional neuroprotective composition which is useful for ameliorating neural dysfunctions such as cardiac ischemia, cerebral ischemia, coronary ischemia, hepatic ischemia, intestinal ischemia, brain ischemia, cerebral infarction, cerebral stroke, transient ischemic attack, mood disorders, dysthymia, major depression, manic depression bipolar disorder, unipolar disorder, mood disorder related to another health condition, substance-induced mood disorder, mental retardation, dyslexia, attention deficit hyperactivity disorder (ADHD), learning deficits and autism.

In another embodiment of the present invention, the neural dysfunction is one or more of depression, autism and/or cerebral ischemia.

The term neural dysfunction also refers to neural abnormalities, neural impairment, behavioral abnormalities and brain dysfunction The therapeutically effective amount of such actives vary depending upon the subject and disease condition being treated, the weight and age of the subject, the severity of the disease condition, the manner of administration and the like, which can readily be determined by one of ordinary skill in the art.

Thus, a "therapeutically effective" amount is an amount that reduces the risk, potential, possibility or occurrence of a disease or disorder, or provides advanced alleviation, mitigation, and/or reduction or restoration of at least one indicator/biomarker (e.g., blood or serum CRP level), and/or minimizes at least one clinical symptom of Ischemia or ASD or MDD.

The 'subject in need thereof' pertains to a subject preferably mammal, more preferably a human suffering from cerebrovascular diseases such as cerebral ischemia, neurodevelopmental disorders such as ASD and mood disorders such as MDD.

In the context of the present invention, the terms "treatment" and the like refer to alleviation, mitigation, prophylaxis, attenuation, management, regulation, modulation, control, minimization, lessening, decrease, down regulation, up regulation, reversal, moderation, prevention, inhibition, stabilization, amelioration, cure, or healing of stroke inducing parameters.

Notably, the present synergistic composition is non-hazardous, non-toxic and safe for human consumption without any side effects. Therefore, the present composition is also used under preventive therapy in healthy subjects.

As used herein, the term "pharmaceutically acceptable carriers, diluents or excipients" is intended to mean, without limitation, any adjuvant, carrier, excipient, sweetening agent, diluents, preservative, dye/colorant, flavor enhancer, surfactant, wetting agent, dispersing agent, suspending agent, stabilizer, isotonic agent, solvent, emulsifier, encapsulating agent, encapsulating polymeric delivery systems or polyethylene glycol matrix, which is acceptable for use in the subject, preferably humans. Excipients also include anti-adherents, antioxidants, binders, coatings, compression aids, disintegrants, dyes (colors), emollients, emulsifiers, fillers (diluents), film formers or coatings, fragrances, glidants (flow enhancers), lubricants, preservatives, sorbents, suspending or dispersing agents, sweeteners, surfactant, anticaking agent, food additives, or waters of hydration, salts.

In another embodiment, the invention relates to a synergistic composition prepared in a manner well known in the pharmaceutical art, and administered by a variety of routes, depending upon whether local or systemic treatment is desired and upon the area to be treated. The preferable route of administration includes but is not limited to sublingual, rectal, topical, parenteral, nasal, or oral. Therapeutic (prescription) supplements are generally administered by the oral, parenteral or nasal routes for curing stroke conditions. The therapeutic administration of compositions of the present invention may be in conjunction with other therapies.

In one embodiment, the present synergistic nutritional composition is administered to a subject in a form suitable for oral use, such as a tablet, capsule (in the form of delayed release, extended release, sustained release, enteric coated release); hard gelatin capsules, soft gelatin capsules in an oily vehicle, granulate for sublingual use, effervescent tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, as tablets, pellets, granules, capsules, lozenges, aqueous or oily solutions, suspensions, emulsions, sprays or reconstituted dry powdered form with a liquid medium or syrup.

In another embodiment, the composition is formulated for parenteral use including intravenous, subcutaneous, intramuscular, intravascular, infusion, intraperitoneal, intracerebral, intracerebroventricular, or intradermal routes of administration. Further, the present synergistic composition is also useful for nasal administration through ion liquid spray device, nasal spray, intranasal spray device, nano-nasal spray, saline spray and like thereof.

In another embodiment of the invention, the diluents are selected from starches, hydrolyzed starches, partially pregelatinized starches, anhydrous lactose, cellulose powder, lactose monohydrate, sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulphate, cellulose acetate, corn starch, pregelatinized starch, dextrin, β-cyclodextrin, dextrates, dextrose, erythritol, ethyl cellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

In a preferred embodiment of the invention, the diluent in the composition/formulation is present in a range of 1% to 30% by weight of the total composition/formulation.

In yet another embodiment of the invention, the binder is selected from disaccharides such as sucrose, lactose, polysaccharides and their derivatives like starches, cellulose or modified cellulose such as microcrystalline cellulose and cellulose ethers such as hydroxypropyl cellulose (HPC); hydroxypropyl methyl cellulose (HPMC); sugar alcohols such as xylitol, sorbitol or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, co-povidone, corn starch, pregelatinized starch, cottonseed oil, dextrates, dextrin, dextrose, ethyl cellulose, guar gum, hydrogenated vegetable oil, mineral oil, hydroxyethyl cellulose, hydroxymethyl cellulose hydroxyl ethyl methyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methylcellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colorants and wax.

In a preferred embodiment of the invention, the binder in the composition/formulation is present in a range of 0.1 to 40% by weight of the composition/formulation.

In a further embodiment of the invention, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulphate, medium-chain triglycerides, mineral oil, myristic acid, palmitic acid, poloxamer, polyethylene glycol, sodium benzoate, sodium chloride, sodium lauryl sulphate, sodium stearyl fumarate, stearic acid, talc, potassium, or sodium benzoate or the like.

In a preferred embodiment of the invention, the lubricant in the composition/formulation is present in a range of 0.1% to 5.0% by weight of the total composition/formulation.

In another embodiment of the invention, the solubilizing agent is selected from polysorbate 80, sodium lauryl sulphate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E, polyethylene glycol succinate, microcrystalline cellulose, carboxymethylcellulose sodium, diethanolamine, ethylene glycol palmitostearate, glycerin monostearate, hypromellose, hypromellose, acetate succinate, lecithin, polyethylene alkyl ethers, aluminum oxide, poly(methylvinyl ether/maleic anhydride), calcium carbonate, crospovidone, cyclodextrins, fructose, hydroxpropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether beta cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, methylparaben, propylparaben, sorbic acid or the like.

In an embodiment of the invention, the amount of solubilizing agent or surfactant in the composition/formulation ranges from 0.1% to 10% by weight of the composition/formulation.

In a preferred embodiment of the invention, the solubilizing agent or surfactant is present in a range of 0.1% to 5.0% by weight of the composition/formulation.

In an embodiment of the invention, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, zinc stearate, magnesium silicate, magnesium trisilicate, silicon dioxide or the like.

In another embodiment of the invention, the amount of glidant present in the composition/formulation ranges from 0.1% to 5.0% by weight of the total composition/formulation.

In some embodiment of the invention, the stabilizers are selected from the group consisting of alginate, agar, carrageen, gelatin, guar gum, gum arabic, locust bean gum, pectin, starch, xanthan gum, trehalose and likewise.

In a preferred embodiment of the invention, the amount of stabilizer in the composition/formulation ranges from 0.1% to 8.0% by weight of the total composition/formulation.

In one embodiment of the invention, the solvent is selected from water, alcohol, isopropyl alcohol, propylene glycol, mineral oil, benzyl alcohol, benzyl benzoate, flavored glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof.

In a preferred embodiment of the invention, the amount of solvent in the composition/formulation is used in a quantity sufficient to make the weight of the composition/formulation 100% by weight.

The additional additives include a polymer, a plasticizer, a sweetener, and a powdered flavor, a preservative, a colorant, a surfactant, and other excipients. The powdered flavor composition includes a flavourant associated with a solid carrier. Coating materials such as synthetic polymers, shellac, corn protein (zein) or other polysaccharides, gelatin, fatty acids, waxes, shellac, plastics, and plant fibers and like thereof are used.

In a preferred embodiment of the invention, the additives are used in a range of 1 to 20% w/w of unit dose.

In another embodiment, the invention provides a synergistic nutritional composition comprising an exogenous blend of agmatine sulphate and nicotinamide riboside chloride along with pharmaceutical excipients, wherein pharmaceutical excipients are selected from a diluent, a binder, a surfactant, a lubricant, a glidant, an additive, a stabilizer or mixtures thereof.

In a preferred embodiment, the diluent is present in a range of 1 to 30%; the binder is present in a range of 0.1 to 30%; the lubricant is present in a range of 0.1 to 5.0%; the glidant is present in a range of 0.1 to 5.0%; the additive is present in a range of 1 to 10%; the surfactant is present in a range of 0.1 to 5.0%; the stabilizer is present in a range of 0.1 to 5.0% by weight of total composition.

In a preferred embodiment, the diluent is present in the range of 1 to 25%; the binder is present in the range of 0.1 to 20%; the lubricant is present in the range of 0.1 to 5.0%; the glidant is present in the range of 0.1 to 3.0%; the additive is present in the range of 1 to 5%; the surfactant is present in the range of 0.1 to 3.0%; the stabilizer is present in the range of 0.1 to 5.0% by weight of total composition.

Advantageously, the present synergistic nutritional composition is non-hazardous, non-toxic and safe for human consumption without any severe side effects and is also used as preventive therapy in healthy subjects.

In a preferred embodiment, the present medicinal composition/formulation is formulated for oral administration. Specifically, the solid medicinal compositions, is in the form of tablets, capsules, pills, hard capsules filled with liquids or solids, soft capsules, sachets, powders, granules, suspensions, solutions or modified release formulations. Formulations of the present invention suitable for oral administration are presented as discrete units such as capsules (e.g., soft-gel capsules, hard-gel capsule), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion.

In a further embodiment, the present composition is formulated in the form of age-appropriate pediatric oral dosage forms such as syrup, minitablets, chewable formulations, orodispersible films orodispersible tablets.

The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 1 mg per day to about 5000 mg per day.

In a preferred embodiment, the total daily dose ranges from about 50 mg per day to about 1500 mg per day.

In some embodiment, the total daily dose administered orally is in a range of about 5 mg to about 2000 mg per day.

In a preferred embodiment, the total daily dose ranges from about 10 mg to about 1000 mg per day.

In an embodiment, the invention provides synergistic nutritional compositions comprising specific combination of agmatine sulphate and nicotinamide riboside chloride thereof along with pharmaceutically acceptable excipients or carriers, wherein the effective unit dose for oral administration is formulated in the range of 25 to 1000 mg.

It is further recommended that children, patients over 60 years old, initially receive low doses and that the dosage be titrated based on individual physiological responses and/or pharmacokinetics. It can be necessary to use dosages outside these ranges in some cases, as will be apparent to those in the art.

The present composition can be used as infant formula as well as adult formula by varying the concentration of active ingredients.

Further, it is noted that the dietician or nutritionist or certified physician knows how and when to interrupt, adjust or terminate therapy in conjunction with an individual patient's response.

The use of any and all examples, or exemplary language (e.g., "such as") provided herein, is intended merely to better illuminate the invention and does not pose a limitation on the scope of the invention unless otherwise claimed.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The invention may be further illustrated by the following examples, which are for illustrative purposes only and should not be construed as limiting the scope of the invention in anyway. The present invention is not to be limited in terms of the particular embodiments described in this application, which are intended as single illustrations of individual aspects of the invention. Functionally equivalent compositions and treatments within the scope of the invention, in addition to those enumerated herein, will be apparent to those skilled in the art from the foregoing description and examples. Such modifications and variations are intended to fall within the scope of the appended claims. The contents of each reference, patent and patent application cited in this application is hereby incorporated by reference in its entirety.

EXAMPLES

Example-1 i. Composition 1: Synergistic Blend

| Ingredients | w/w % |
|---|---|
| Agmatine Sulphate (decarboxylated L-arginine) | 50%-90% |
| Sirtuin 1 activators | 10%-50% | ii. Composition 2: Tablet/Capsule

| Ingredients | w/w % unit dose |
|---|---|
| Agmatine Sulphate | 70 ± 10% |
| Nicotinamide riboside chloride | 15 ± 5% |
| Excipients | 10-20% |
| Average Weight (%) | 100% |
| Average weight in mg | 300-400 mg | iii. Composition 3: Tablet/Capsule

| Ingredients | w/w % unit dose |
|---|---|
| Agmatine Sulphate | 75 ± 5% |
| Nicotinamide riboside chloride | 15 ± 5% |
| Excipients | 10-20% |
| Average Weight (%) | 100% |
| Average weight in mg | 600-700 mg | iv. Composition 4: Tablet/Capsule

| Ingredient | w/w % unit dose |
|---|---|
| Agmatine Sulphate | 68 ± 10% |
| Nicotinamide riboside chloride | 20 ± 5% |
| Excipients | 10-20% |
| Average Weight | 100% |
| Average weight in mg | 700-800 mg | v. Composition 5: Tablet/Capsule

| Ingredients | w/w % unit dose |
|---|---|
| Agmatine Sulphate | 62.5% |
| Nicotinamide riboside chloride | 18.5% |
| Diluents | 1-10% |
| Binders | 0.5-5% |
| Glidants | 0.5-5% |
| Lubricants | 0.5-5% |
| Stabilizers | 0.1-10% |
| Additives | 1-10% |
| Solvents | QS | vi. Composition 6: Tablet/Capsule

| Ingredients | w/w % unit dose |
|---|---|
| Agmatine Sulphate | 70% |
| Nicotinamide riboside chloride | 18% |
| Diluent | 1-20% |
| Binder | 0.1-5% |
| Glidant | 0.1-5% |
| Lubricants | 0.5-5% |
| Additives | 1-10% |
| Solvent | QS | vii. Composition 7: Tablet/Capsule

| Ingredients | mg per unit dose |
|---|---|
| Agmatine Sulphate | 500 |
| Nicotinamide riboside chloride | 150 |
| Microcrystalline Cellulose | 1-20 |
| Silicon dioxide | 1-10 |
| Hydroxypropyl Methylcellulose | 1-10 |
| Zinc Stearate | 1-10 |
| PVP K-30 | 5-10 |
| Talc | 1-10 |
| Polysorbate 80 | 1-10 |
| Mannitol | 1-20 |
| Propylene Glycol | QS |
| Water | QS |
| Average weight | 700-800 mg | viii. Composition 8: Tablet/Capsule

| Ingredients | mg per unit dose |
|---|---|
| Agmatine Sulphate | 500 |
| Nicotinamide riboside chloride | 300 |
| Sodium ascorbate | 1-10 |
| Microcrystalline Cellulose | 2-20 |
| Silicon dioxide | 5-15 |
| Hydroxypropyl Methylcellulose | 2-10 |
| Magnesium Stearate | 2-10 |
| PVP K-30 | 5-10 |
| Talc | 1-10 |
| Polysorbate 80 | 5-20 |
| Mannitol | 5-20 |
| Alcohol | QS |
| Water | QS |
| Average weight | 800-900 mg | ix. Composition 9: Syrup

| Ingredients | mg per 5 ml |
|---|---|
| Agmatine Sulphate | 250 |
| Nicotinamide riboside chloride | 50 |
| Sucrose | 1-10 |
| Sodium ascorbate | 1-10 |
| Water | QS |
| Flavours | QS | x. Composition 10: Tablet/Capsule

| Ingredients | mg per unit dose |
|---|---|
| Agmatine Sulphate | 500 |
| Nicotinamide riboside chloride | 125 |
| Ascorbic acid | 1-10 |
| Microcrystalline Cellulose | 1-10 |
| Silicon dioxide | 1-10 |
| Hydroxypropyl Methylcellulose | 1-10 |
| Magnesium Stearate | 2-10 |
| Polyvinylpyrrolidone | 1-10 |
| Talc | 1-10 |

| Ingredients | mg per unit dose |
|---|---|
| Polysorbate 80 | 1-10 |
| Mannitol | 1-10 |
| IPA | QS |
| Water | QS |
| Average weight | 650-700 mg |

Example 2: Animal Study

To Assess the Neuroprotective Effect of Test Product Against Global Ischemia Reperfusion Induced Brain Injury (Cerebral Infarction) in Wistar Rats
Test System and Animal Husbandry
Species: Rats
Strain: Wistar
Sex: Male
No. of animals: 36 Animals (n=6 per group)
Body weight: 200-220 gms
CPCSEA Registration Number-1803/PO/RcBi/S/2015/CPCSEA
Animal House Conditions
Lighting: 12/12 hour light-dark cycle
Temperature: 22±3° C.
Relative Humidity: 30 to 70%
Animals had continuous access to fresh, potable, uncontaminated drinking water.
Feed: Normal chow diet [PURINA 5L79 from PMI Nutritional, USA]
Group, Designation and Dose Levels:

TABLE 1

Animal grouping and treatment details

| Groups | Group Description | Treatment Description | No. of animals |
|---|---|---|---|
| Group 1 | Normal Control (Without Exposure of Ischemia Reperfusion) | 0.5% Carboxy Methyl Cellulose (CMC) | 06 |
| Group 2 | Ischemia Reperfusion (I/R) Control + Exposure of Ischemia Reperfusion | 0.5% CMC | 06 |
| Group 3 | Standard (Cerebroprotein hydrolysate Tablet) + Exposure of Ischemia Reperfusion | 9.3 mg/kg | 06 |
| Group 4 | Agmatine Sulphate + Exposure of Ischemia Reperfusion | 103.33 mg/kg | 06 |
| Group 5 | Nicotinamide Riboside chloride + Exposure of Ischemia Reperfusion | 31 mg/kg | 06 |
| Group 6 | Agmatine Sulphate + Nicotinamide Riboside chloride + Exposure of Ischemia Reperfusion | 103.33 mg/kg + 31 mg/kg | 06 |

Test Items, Vehicle and Formulation Details
Test item: G4, G5, G6
Dose: G4—103.33 mg/kg; G5-31 mg/kg; G6—103.33 mg/kg+31 mg/kg
Route: Oral route (p.o)
Frequency: Daily
Experimental Procedure:
Animals were divided into six groups; each group consists of 6 animals. Group 1 was served as a Normal control and treated with vehicle 0.5% CMC; Group 2 was served as Ischemia Reperfusion control and treated with vehicle 0.5% CMC, whereas Group 3 was treated with standard product (Cerebroprotein hydrolysate). Group 4 and Group 5 received test sample AGM sulphate and test sample Nicotinamide riboside chloride respectively. Group 6 received test sample comprising a combination of AGM sulphate and nicotinamide riboside chloride. Treatment was given orally for 10 days. Test substances agmatine sulphate (103.33 mg/kg), Nicotinamide riboside chloride (31 mg/kg), agmatine sulphate+Nicotinamide riboside chloride (103.33 mg/kg+31 mg/kg), were administered orally for 10 days. At the end of the experimental period, blood was collected for biochemical analyses and animals were sacrificed for histological analysis.

On the $7^{th}$ day, all the experimental animals, excluding Group 1, were exposed to ischemia followed by 72 hours of reperfusion along with treatment. After 72 hours of reperfusion, the animals were euthanized by isoflurane until breathing stopped. The rats were decapitated immediately, and their brains were extracted for biochemistry and TTC staining. The results of the test substances showed effective prevention of neuron cells from death caused by cerebral ischemia or reperfusion to protect from brain damage.

i. Induction of Cerebral Infarction:

Induction of Global cerebral ischemia/reperfusion was carried out using the standard method. The rats were anaesthetized with an i.p. co-injection of ketamine (85 mg/kg) and xylazine (15 mg/kg) and a midline ventral incision was made in the throat. Right and left common carotid arteries were located and freed from surrounding tissue and vagus nerve. A cotton thread was passed below each artery. Global cerebral ischemia was induced by occluding the carotid arteries with a knot. After 30 minutes of global cerebral ischemia, the cotton thread was removed with the help of two knot releasers to allow the reperfusion of blood through carotid arteries for 72 hours. All surgical procedures were carried out under aseptic and sterile condition.

ii. Tetrazolium Chloride Staining (TTC Staining):

The rats were anesthetized and were given cardiac perfusion with 100 ml cold saline. The brains were carefully removed. The brains were frozen at −20° C. for 20 min, and then cut from the anterior pole into five coronal slices of 2 mm thickness. The slices were stained with 2% 2, 3, 5-triphenyl tetrazolium chloride solution in the dark at 37° C. in an incubator for 30 minutes and turned over every 5 minutes. A 10% buffered-formalin solution was used for fixation (24 hours) prior to imaging. The normal brain tissue was stained red, whereas the ischemic area remained unstained.

iii. Statistical Analysis

The values were expressed in Mean±sem. The significance of in vivo data was analyzed by one way Anova followed by Dunnet test. P<0.05 was considered as significant.

Results:

TABLE 2

Effect of test substances on Rat TNF alpha Level
TNF alpha Level (pg/ml)

| Group | Treatment | TNF alpha |
|---|---|---|
| Group 1 | Normal Control (0.5% CMC) | 71.17 ± 3.48 |
| Group 2 | Positive Control (0.5% CMC) | 172.17 ± 6.35 |
| Group 3 | Standard (9.3 mg/kg) | 109.00 ± 3.02*** |
| Group 4 | Agmatine sulphate (103.33 mg/kg) | 142.00 ± 1.53*** |
| Group 5 | Nicotinamide Riboside chloride (31 mg/kg) | 160.33 ± 4.79* |

TABLE 2-continued

Effect of test substances on Rat TNF alpha Level
TNF alpha Level (pg/ml)

| Group | Treatment | TNF alpha |
|---|---|---|
| Group 6 | Agmatine sulphate (103.33 mg/kg) + Nicotinamide Riboside chloride (31 mg/kg) | 112.17 ± 4.07*** |

Values were expressed as mean ± SEM (n = 6), Statistical significance are compared between Ischemic Reperfusion control (Group 2) versus other treatment groups (G1, G3, G4, G5, G6)
(*P Value < 0.05;
** P Value < 0.001;
***P Value < 0.0001).

TABLE 3

Effect of test substances on Rat Interleukin - 6 Levels
Interleukin - 6 Levels (pg/ml)

| Group | Treatment | Interleukin - 6 |
|---|---|---|
| Group 1 | Normal Control (0.5% CMC) | 41.67 ± 1.37 |
| Group 2 | Positive Control (0.5% CMC) | 121.83 ± 1.65 |
| Group 3 | Standard (9.3 mg/kg) | 67.00 ± 1.21*** |
| Group 4 | Agmatine sulphate (103.33 mg/kg) | 91.39 ± 0.92*** |
| Group 5 | Nicotinamide Riboside chloride (31 mg/kg) | 109.56 ± 0.27*** |
| Group 6 | Agmatine sulphate (103.33 mg/kg) + Nicotinamide Riboside chloride (31 mg/kg) | 69.56 ± 2.24*** |

Values were expressed as mean ± SEM (n = 6), Statistical significance are compared between Ischemic Reperfusion control (Group 2) versus other treatment groups (G1, G3, G4, G5, G6)
(* P Value < 0.05;
** P Value < 0.001;
***P Value < 0.0001).

Discussion

Cerebral ischemia causes dizziness, double vision, difficulty in speaking or slurred speech, loss of body coordination and sometimes paralysis, and if it remains untreated it will result in unconsciousness or permanent damage to the brain or death.

The present investigation demonstrated the neuroprotective activity of test substances against Global Ischemia Reperfusion Induced Brain Injury (Cerebral Infarction) in Wistar Rats. No significant change in body weight was observed in all the remaining groups when compared with Ischemia Reperfusion Control group (G2).

Figure 2:
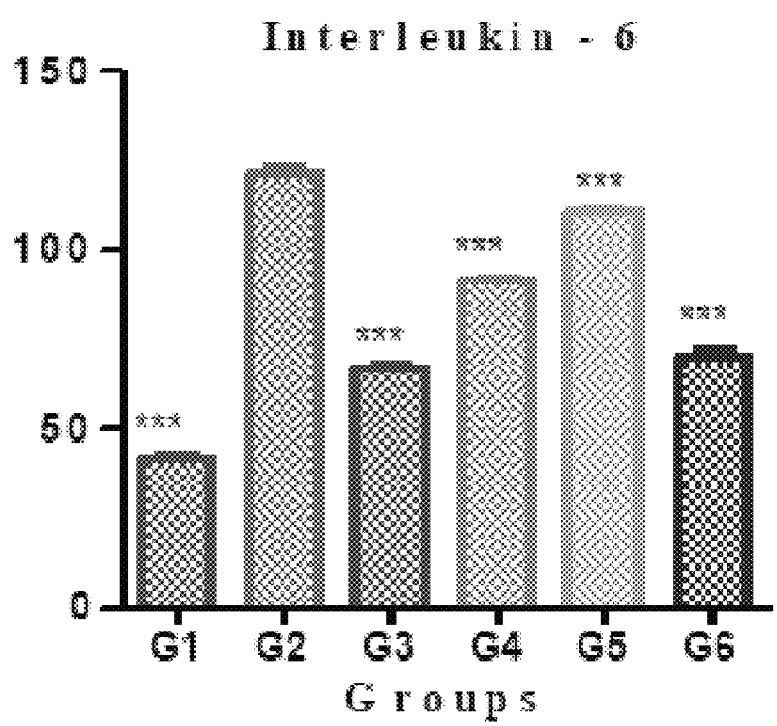
FIG. 2 illustrates the effect of test substances on Rat Interleukin-6 (IL-6) levels

Table 2 & FIG. 1 represent the TNF alpha levels showing significant decrease in the test substances treated group when compared with Ischemia Reperfusion Control group (G2). Interleukin—6 levels showed significant decrease in the test substances treated group when compared with Ischemia Reperfusion Control group (G2) (Table 3 & FIG. 2).

Figure 3:
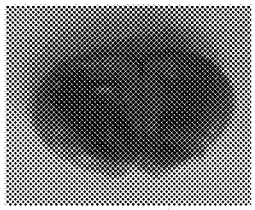
FIG. 3 illustrates the effect of test substances on Rat TTC staining—Group 1—Normal Control [RA-01 to RA-06 represent Rat model]
Figure 4:
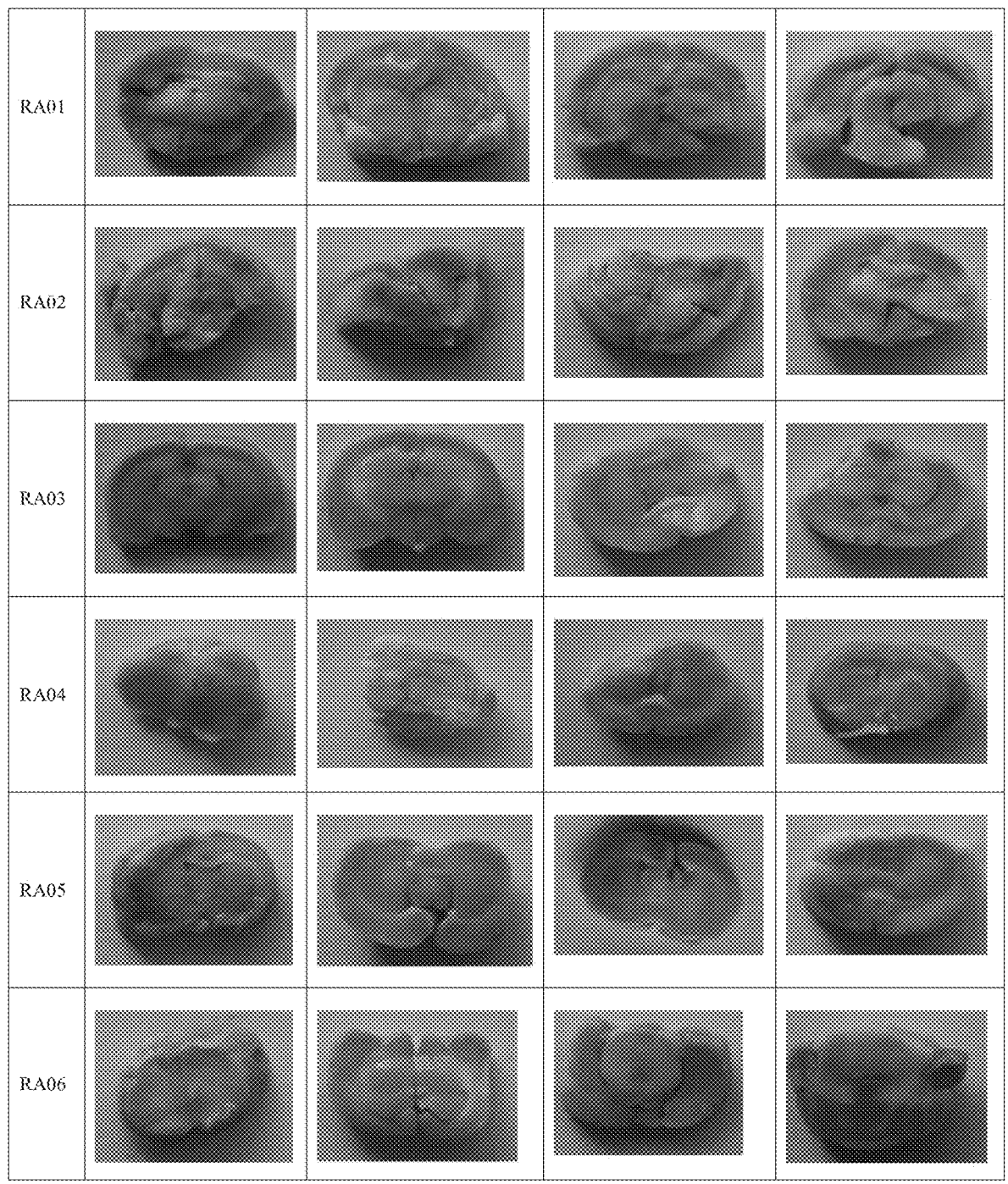
FIG. 4 illustrates the effect of test substances on Rat TTC staining—Group 2—Positive Control
Figure 5:
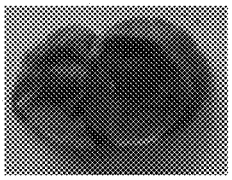
FIG. 5 illustrates the effect of test substances on Rat TTC staining—Group 3—Standard Cerebroprotein hydrolysate (Tablet)
Figure 5:
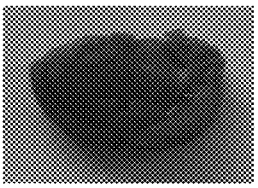
Figure 5:
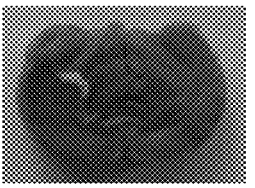
Figure 5:
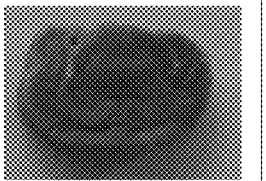
Figure 5:
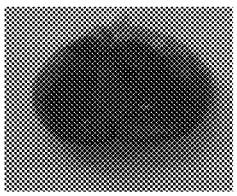
Figure 5:
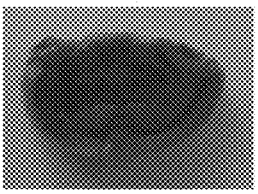
Figure 5:
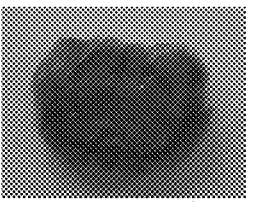
Figure 5:
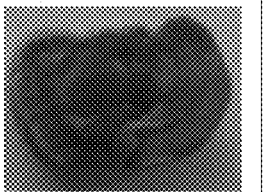
Figure 5:
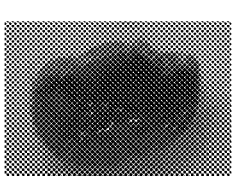
Figure 5:
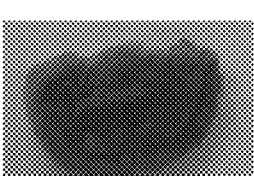
Figure 5:
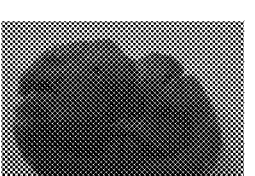
Figure 5:
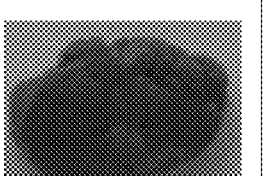
Figure 5:
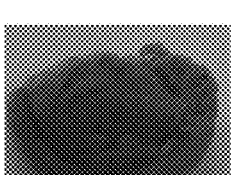
Figure 5:
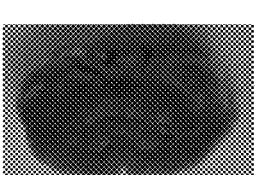
Figure 5:
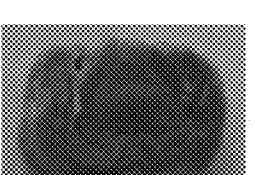
Figure 5:
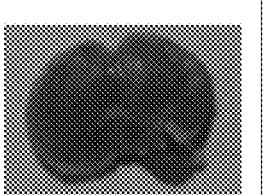
Figure 5:
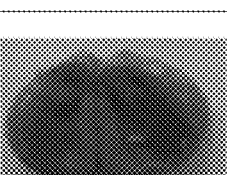
Figure 5:
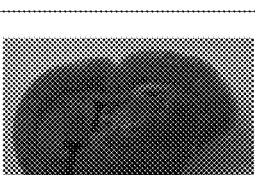
Figure 5:
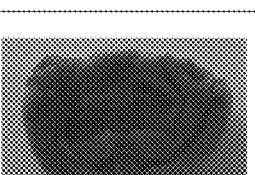
Figure 5:
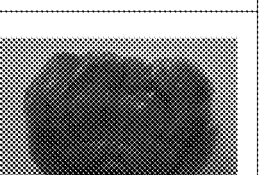
Figure 5:
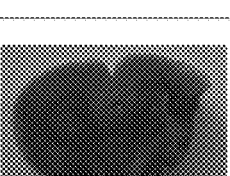
Figure 5:
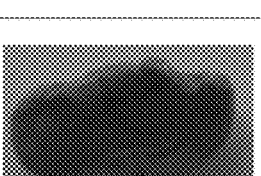
Figure 5:
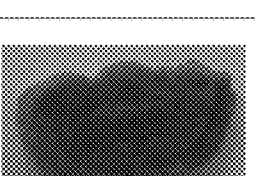
Figure 5:
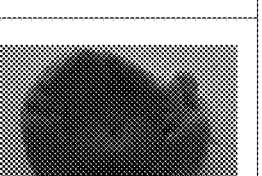
Figure 6:
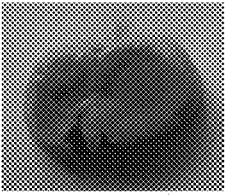
FIG. 6 illustrates the effect of test substances on Rat TTC staining—Group 4—(Agmatine Sulphate)
Figure 6:
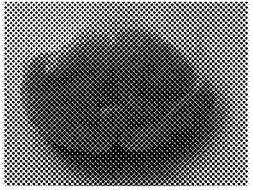
Figure 6:
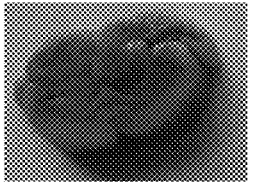
Figure 6:
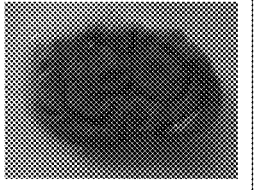
Figure 6:
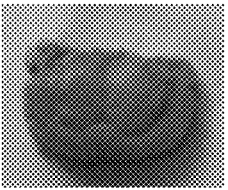
Figure 6:
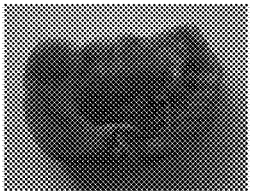
Figure 6:
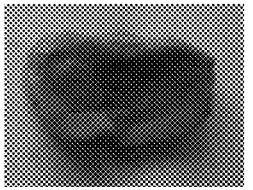
Figure 6:
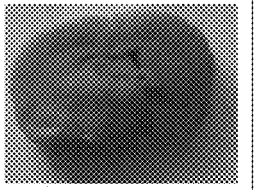
Figure 6:
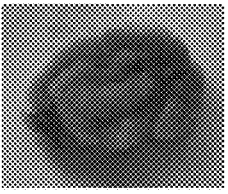
Figure 6:
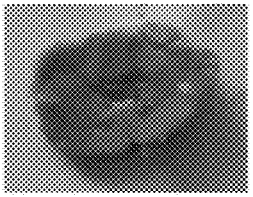
Figure 6:
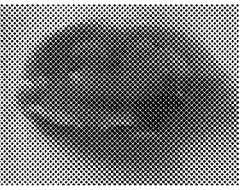
Figure 6:
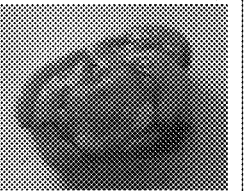
Figure 6:
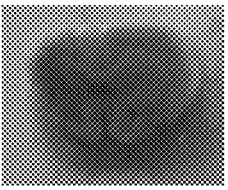
Figure 6:
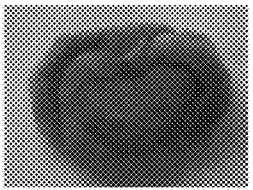
Figure 6:
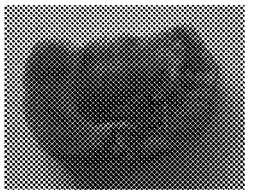
Figure 6:
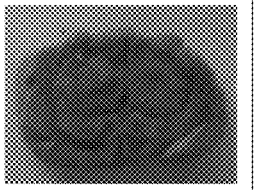
Figure 6:
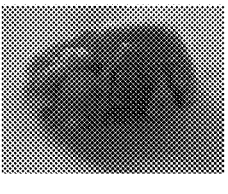
Figure 6:
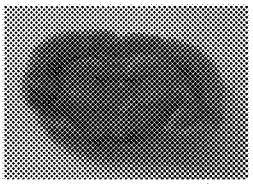
Figure 6:
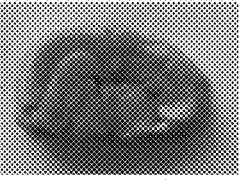
Figure 6:
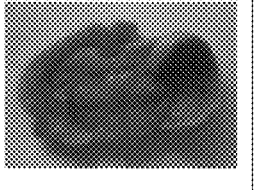
Figure 6:
Figure 6:
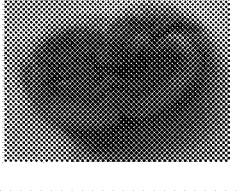
Figure 6:
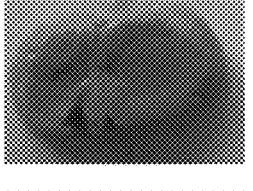
Figure 6:
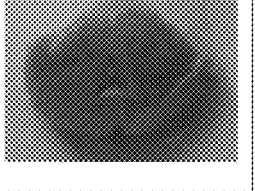
Figure 7:
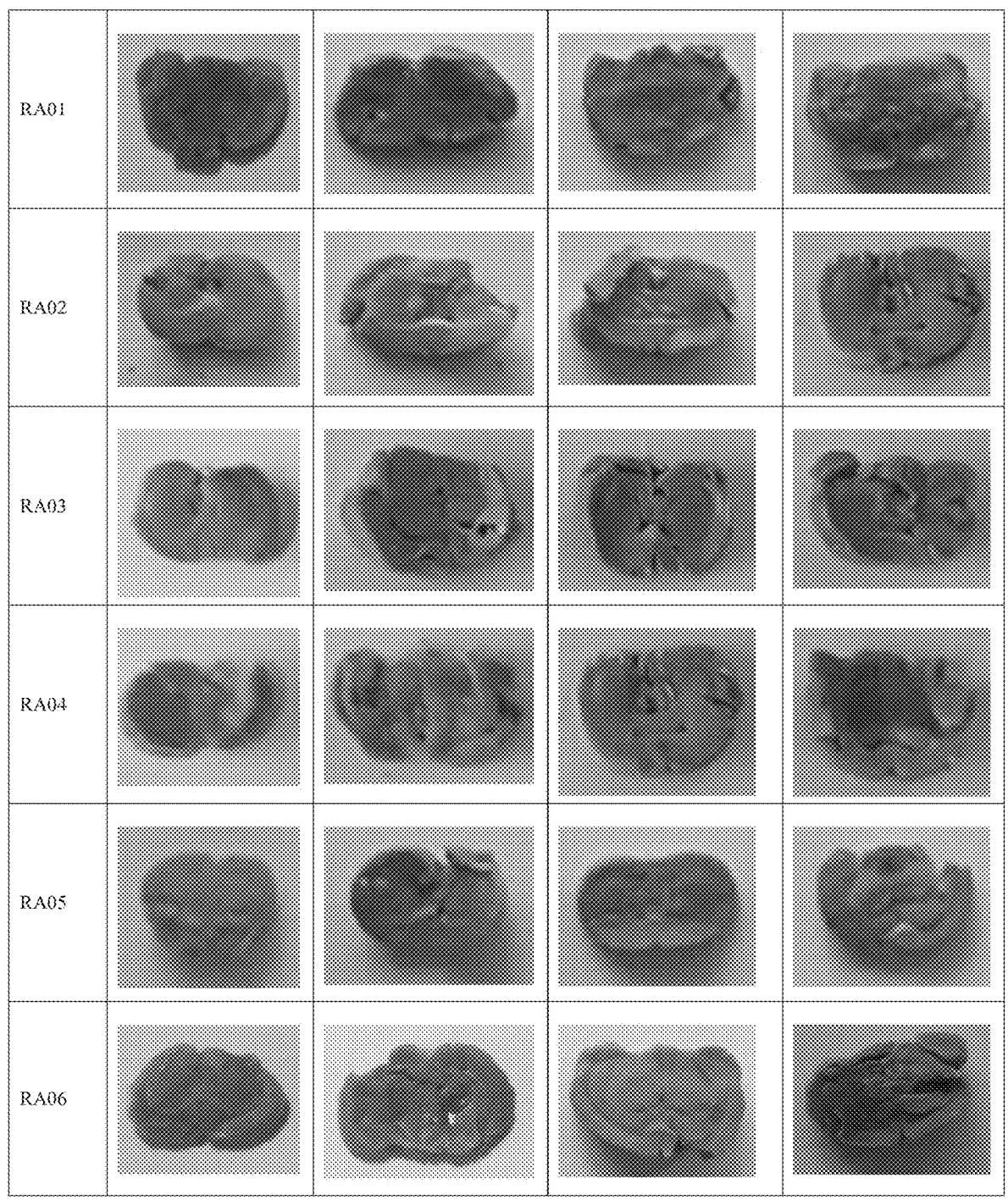
FIG. 7 illustrates the effect of test substances on Rat TTC staining—Group 5—(Nicotinamide riboside chloride)
Figure 8:
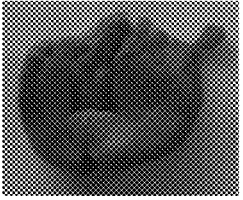
FIG. 8 illustrates the effect of test substances on Rat TTC staining—Group 6—(combination agmatine sulphate+nicotinamide riboside chloride)
Figure 8:
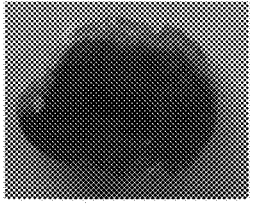
Figure 8:
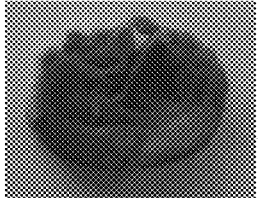
Figure 8:
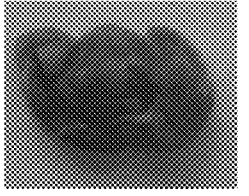
Figure 8:
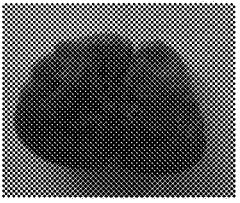
Figure 8:
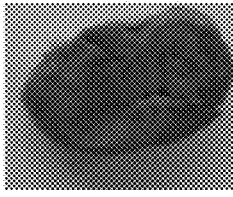
Figure 8:
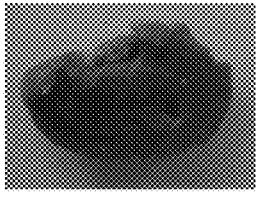
Figure 8:
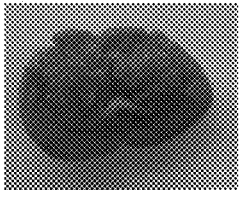
Figure 8:
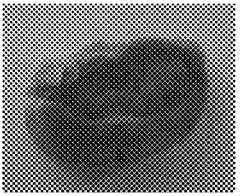
Figure 8:
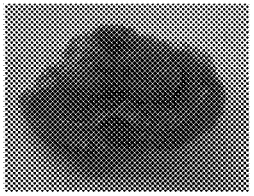
Figure 8:
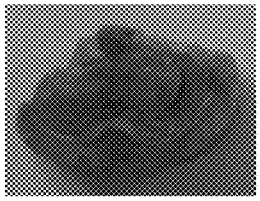
Figure 8:
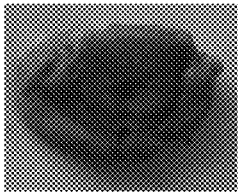
Figure 8:
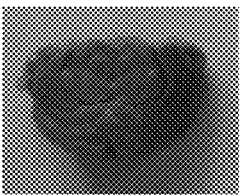
Figure 8:
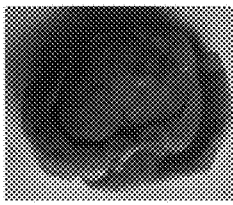
Figure 8:
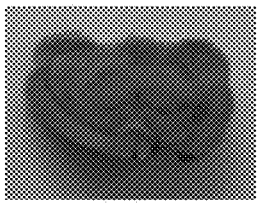
Figure 8:
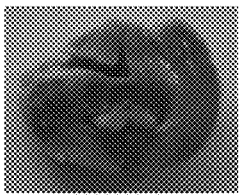
Figure 8:
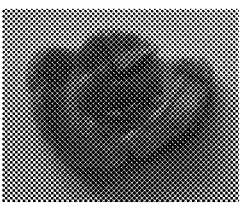
Figure 8:
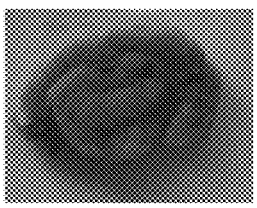
Figure 8:
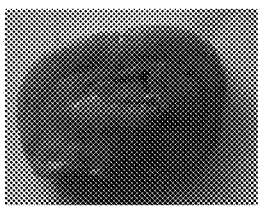
Figure 8:
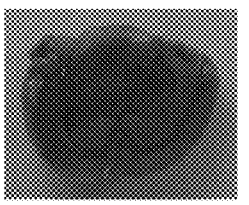
Figure 8:
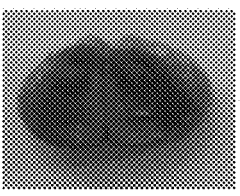
Figure 8:
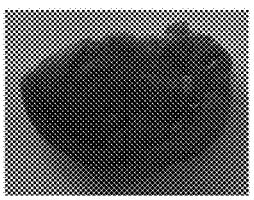
Figure 8:
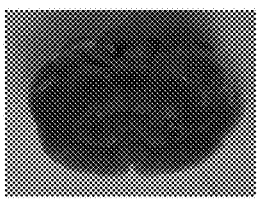
Figure 8:
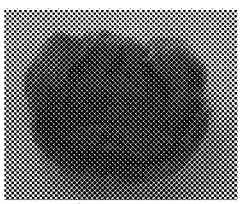
Figure 9:
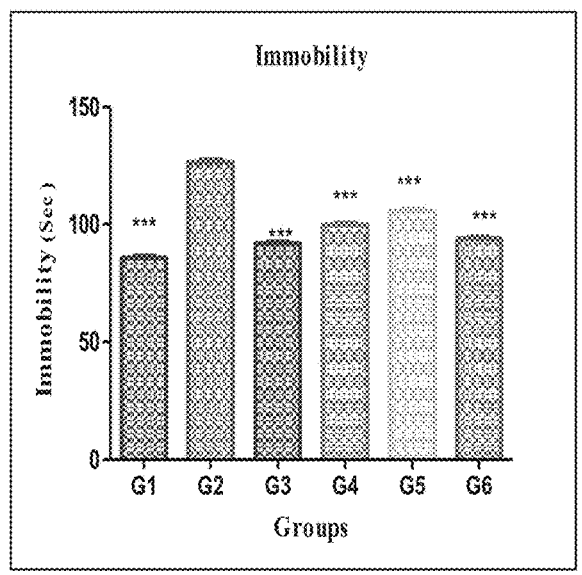
FIG. 9 illustrates the effect of test substance on behavior on rats (a) Immobility (b) Swimming (c) Climbing (d) Open field test forming part of the MDD study
Figure 9:
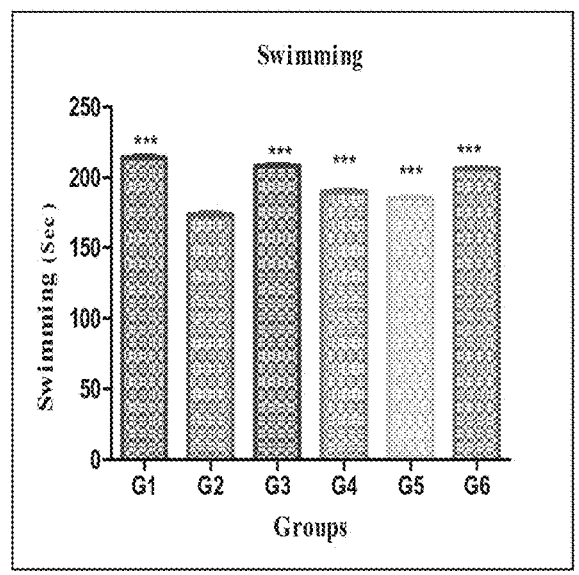
Figure 9:
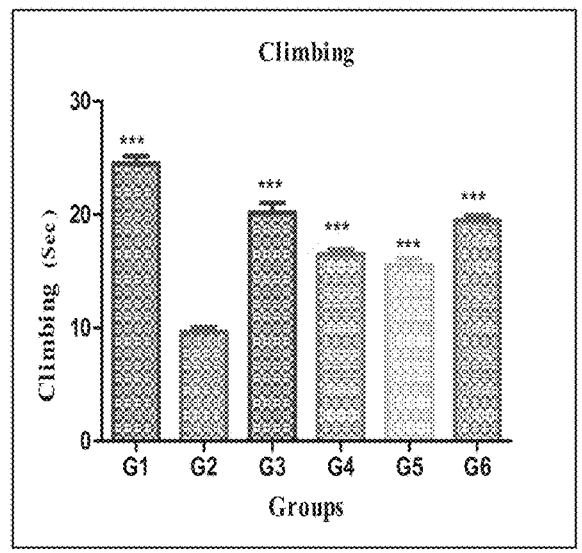
Figure 9:
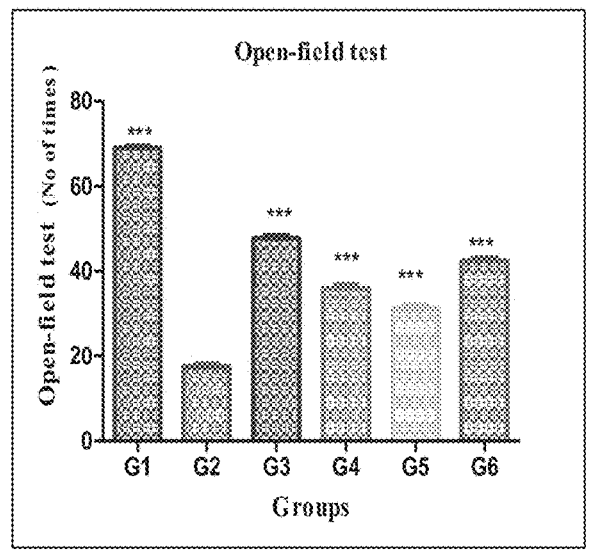

FIG. 3 (Group 1-6) represent the Tetrazolium chloride staining (TTC) of brain tissue of animals showing normal brain tissue was stained red, whereas ischemic area remained unstained.

Conclusion

In the present study, the model of global ischemia reperfusion induced brain injury (cerebral infarction) was performed in rats. The brain infarct area, biochemical parameters and histopathology of normal and treated rats with cerebral ischemia or reperfusion injury were investigated to find out how the test substances to protect and improve the brain function. The results showed that these test substances could significantly reduce relative inflammation in brain and rescue neural dysfunction effectively.

It is concluded that, the test substance i.e., combination of Agmatine sulphate+nicotinamide riboside chloride (G6) effectively prevents neuron cells from death caused by cerebral ischemia or reperfusion and protects the cells from brain damage as compared to individual dose of Agmatine sulphate or nicotinamide riboside chloride.

Example 3

"Evaluation of Test Substances Against Major Depression Disorder in Wistar Rats"

The aim of this study was to evaluate the effect of test substances on Major depression disorder in wistar rats. Test samples were administrated orally for 7 days at a dose level of test substance agmatine sulphate (51.67 mg/kg), nicotinamide riboside chloride (12.92 mg/kg) and agmatine sulphate+nicotinamide riboside chloride (51.67+12.92 mg/kg) according to the body weight of animals. On the days of the experiment, all the animals were forced to swim (Forced swim test) individually to measure the first occurrence of immobility, duration of immobility, total time spent in active swimming and latency to exhaustion. The rats were made to swim in a cylindrical vessel filled with water up to 30 cms at 25° C. All the animals were trained the day before for 15 minutes as pre-test swim followed by 5 minutes test swim session on the next day and immobility was scored and recorded. The rats were removed after the swim session and they were returned to their cages after 20 minutes. The ambulatory behavior was assessed by using an instrument consisting of a wooden box (40 cm×60 cm×50 cm) with its floor divided into 12 equal rectangles. The rats were placed in the left corner. The rats crossed the rectangular part with all the paws. The number of rectangles crossed by each rat in a 6 minute session with all the paws were recorder. The instrument was cleaned in between of each test with 10% ethanol to avoid contamination.

Animal House Conditions—
Test System and Animal Husbandry
Test Species: Rats
Strain: Albino wistar
Sex: Male
Age: 8-10 Weeks
Body Weight: 180-200 gms
Source: In house breed
CPCSEA Registration Number-1803/PO/RcBi/S/2015/CPCSEA
Animal House Conditions
Lighting: 12/12 hour light-dark cycle
Temperature: 22±3° C.
Relative Humidity: 30 to 70%
Animals had continuous access to fresh, potable, uncontaminated drinking water.
Feed: Normal chow diet [Amrut Feeds, Krishna valley Agrotech LLP, Source: Prashanth Enterprises, Pune]
The study was commenced after the protocol reviewed and approved by Institutional Animal Ethical Committee (IAEC) of Radiant Research Services Pvt. Ltd

TABLE 4

Test items, Vehicle and Formulation details

| Test item | G4 (Agmatine sulphate) | G5 (Nicotinamide Riboside chloride) |
|---|---|---|
| Dose | 51.67 mg/kg | 12.92 mg/kg |
| Route | Oral | Oral |

TABLE 4-continued

Test items, Vehicle and Formulation details

| Test item | G4 (Agmatine sulphate) | G5 (Nicotinamide Riboside chloride) |
|---|---|---|
| Frequency | Daily for 7 days. | Daily for 7 days. |
| Vehicle | 0.5% Carboxy Methyl Cellulose sodium | 0.5% Carboxy Methyl Cellulose sodium |

TABLE 5

Group, Designation and Dose Levels

| Groups | Group Description | Treatment | Dose Level | Dose Volume (ml/kg) | No. of animals |
|---|---|---|---|---|---|
| Group-1 | Normal Control | 0.5% CMC | 0.0 mg/kg (Vehicle) | 10 ml | 6 |
| Group-2 | Disease control | Normal saline | Normal Saline | 10 ml | 6 |
| Group-3 | Standard | Escitalopram | 20.07 mg/kg | 10 ml | 6 |
| Group-4 | Test 1 | Agmatine Sulphate | 51.67 mg/kg Bodyweight | 10 ml | 6 |
| Group-5 | Test 2 | Nicotinamide Riboside chloride | 12.92 mg/kg Bodyweight | 10 ml | 6 |
| Group-6 | Test 1 + Test 2 | Agmatine Sulphate + Nicotinamide Riboside chloride | 51.67 mg + 12.92 mg/kg | 10 ml | 6 |

Study Procedure

All the animals were divided into six groups and each group consisted of six animals. Group 1 served as normal control and was treated with 0.5% CMC, Group 2 served as Positive Control and was treated with 0.5% CMC, whereas Group 3 was treated with Standard product Escitalopram (20.07 mg/kg b.w). Groups 4, 5 and 6 served as test substances treated groups and received test substances at a dose levels of 51.67 mg/kg (Agmatine Sulphate), 12.92 mg/kg (Nicotinamide Riboside chloride), and 51.67+12.92 mg/kg (Agmatine Sulphate+Nicotinamide Riboside chloride). All animals were acclimatized for seven days and depression was induced by administering Reserpine 1.0 mg/kg body once per day for 10 days except normal control group. Normal control group was injected with phosphate buffer solution. The Reserpine treated animals were divided into five groups. Each group contained six animals and were treated orally as follows. The dose was administered for 7 Days after acclimatisation. All the groups except Normal control and Positive control group were treated with test substances for 7 days. During the treatment each animal was forced to swim individually for 5 minutes in a glass jar of height 20 cms, diameter 10 cms, and filled with fresh water to a depth of 30 cms with the water being maintained at room temperature. The parameters measured were first occurrence of immobility (the period the animal swims continuously before the first pause of swimming activity), duration of immobility (the total time during which the animal is immobile), total time spent in active swimming (the total duration during which the animal swims throughout the experimental period), and latency to exhaustion (the period when the animal starts to sink).

Dose Administration:

The test formulations were administered once each day by oral route at the dose levels of 51.67 mg/kg (Agmatine Sulphate), 12.92 mg/kg (Nicotinamide Riboside chloride) and 51.67+12.92 mg/kg (Agmatine Sulphate+Nicotinamide Riboside chloride), to rats of corresponding groups for a minimum of 7 consecutive days at approximately same time each day (±1 hour). The dose volume administered to each rat was 10 ml/kg/day. Similarly, vehicle for vehicle control and positive control groups were administered orally at the same dose volume for a minimum of 7 consecutive days. The dose volume was calculated for individual animals on the first day of the treatment and was re-calculated according to the recent body weights recorded during the study. Daily individual dose volumes were recorded in the study records.

Results:

Behavioural Observation

A. Forced Swim Test

In the forced swim test, the behavior of all the animals were evaluated and recorded. The recordings included results of immobility, climbing and active swimming analysis. The immobility of the animals in the test substance treated groups was reduced (showing better effect) compared to that of disease control group. The mobility of the animals in the treatment groups increased after being treated with the test substance Agmatine Sulphate and Nicotinamide Riboside chloride. The animals in Group 6 (Agmatine Sulphate+Nicotinamide Riboside chloride) showed better mobility than Group 4 (Agmatine Sulphate) & 5 (Nicotinamide Riboside chloride). The climbing behavior and total active swimming showed increase activity in treatment groups when compared to the disease control.

B. Open Field Test

In the open field test, all the animals were observed for the evaluation of ambulatory movement. The number of open arm entries were observed, recorded and analyzed. The result of the open field test shows that increase in ambulatory effect of treated group animals compared to that of disease control. Group 6 (Agmatine Sulphate+Nicotinamide Riboside chloride) showed higher increase in the ambulatory effect compared to the Groups 4 and 5.

TABLE 6

Effect of test substance on Rat physical parameters
Physical Parameters

| Group | Treatment | Immobility | Climbing | Total time spent in active swimming (Sec) |
|---|---|---|---|---|
| Group 1 | Normal Control | 85.67 ± 0.80 | 24.50 ± 0.67 | 214.33 ± 0.80 |
| Group 2 | Disease Control | 126.50 ± 1.06 | 9.67 ± 0.42 | 173.50 ± 1.06 |
| Group 3 | Standard-Escitalopram | 91.67 ± 0.80 | 20.17 ± 0.87 | 208.33 ± 0.80 |
| Group 4 | Test I | 99.67 ± 0.67 | 16.50 ± 0.43 | 190.17 ± 0.79 |
| Group 5 | Test II | 105.50 ± 0.85 | 15.50 ± 0.62 | 185.33 ± 0.67 |
| Group 6 | Test III | 93.83 ± 0.75 | 19.50 ± 0.43 | 206.17 ± 0.75 |

Values were expressed as mean ± SEM (n = 6), Statistical significance are compared between Disease Control (Group 2) versus other treatment groups (G1, G3, G4, G5 & G6)
(* P Value < 0.05;
** P Value < 0.001;
*** P Value < 0.0001).

TABLE 7

Effect of test substance on Rat physical parameters
Open Arm entries (Open field test)

| Group | Treatment | No. of open arm entries |
|---|---|---|
| Group 1 | Normal Control | 69.00 ± 0.52 |
| Group 2 | Disease Control | 17.50 ± 0.56 |
| Group 3 | Standard (Escitalopram) | 47.83 ± 0.60 |
| Group 4 | Test I | 36.00 ± 0.86 |
| Group 5 | Test II | 31.33 ± 0.71 |
| Group 6 | Test III | 42.50 ± 0.76 |

Values were expressed as mean ± SEM (n = 6), Statistical significance are compared between Disease Control (Group 2) versus other treatment groups (G1, G3, G4, G5 & G6)
(* P Value < 0.05;
** P Value < 0.001;
*** P Value < 0.0001).

Discussion

The present study was conducted to evaluate the effect of test substances on major depression disorder in Wistar rats. The depression was induced by repeated administration of the Reserpine at the dose of 1.0 mg/kg body weight. All the animals were divided into six groups and each group contained six animals. Except normal control group, all the remaining groups of animals were treated with Reserpine daily up to 10 days to induce depression. During the Reserpine treatment all the animals were monitored and observations were recorded. During the induction period, the depressive effect of the drug (Reserpine) was observed and the behavior of the Reserpine induced animals was evaluated by using the forced swim test. Forced swim test is used to face validation of depression in animal models. After the induction of depression, except the normal control (Reserpine treated) group, animals were divided into five groups which included group 2 (Disease control), Group 3 (Standard control) Group 4 (Test I), Group 5 (Test II) and Group 6 (Test I+II). Groups 1 and 2 were treated with the Vehicle (0.5% CMC), Group 3 was treated with the Reference standard drug (Escitalopram), the Group 4 was treated with the test substance (Agmatine Sulphate), Group 5 was treated with the test substance (Nicotinamide Ribosome Chloride), and Group 6 was treated with the test substance (Agmatine Sulphate+Nicotinamide Ribosome Chloride) for 7 Consecutive days. The behavioral observations were evaluated and recorded. The behavioral observations were evaluated by using the forced swim test and open field test. In the forced swim test, all the treated animals including the Reserpine treated animals (positive control) and the Normal control group were forced to swim for the evaluation of effect of test substance for a period of 5 minutes (test swim), and latency period and immobility of the animals were recorded. The results obtained in the forced swim test were compared to that of normal control and positive control. In the open field test, the ambulatory behavior was evaluated and recorded. In this test, the instrument consisting of a wooden box (40 cm×60 cm×50 cm) and its floor divided into 12 equal rectangles was used and the rats were placed in the left corner. The rats crossed the rectangular part with all the paws. The entries of arms were recorded and calculated. The results obtained in the open field test were compared to that of normal control, positive and standard control groups. The present study indicates that the test substance I (Agmatine Sulphate) and II (Nicotinamide Ribosome Chloride) showed positive effects on major depression disorder and when the animals were treated with test substances in combination (Agmatine Sulphate+Nicotinamide Riboside chloride), it showed higher efficacy than individual therapy.

Conclusion

Based on the overall study, results obtained in the behavioral evaluation tests provided evidence that the combination test substance G6 (Agmatine Sulphate+Nicotinamide Riboside chloride) showed better activity than that of individual test substance administration.

Example 4

"Evaluation of the Effect of Test Substance on Valproic Acid-Induced Autism Disorder in Albino Wistar Rats"

The present study was to evaluate the effect of test substances on Valproic acid induced Autism spectrum disorder in wistar rats. The animals (50 animals) were divided into five groups each group consisting of 10 animals (5 animals per sex). Animals in Group-1 were treated with vehicle (0.5% CMC), Group-2 was treated with Valproic acid (VPA) 400 mg/kg via subcutaneous route, Group-3, Group-4 and Group-5 were treated with test substance Agmatine Sulphate (25.83 mg/kg), Nicotinamide Riboside chloride (6.46 mg/kg) and Agmatine Sulphate+Nicotinamide Riboside chloride (25.83 mg/kg+6.46 mg/kg) respectively, according to the body weight of animals. At the end of the experimental period, blood was collected from each group for biochemical analyses. On postnatal day 40 (PND 40), all the animals were exposed to the Morris water maze test and Open field test for specific time periods to determine the autism-like behaviors of the test substances. The present study showed that test substance treated groups improved autistic like behavioral activities compared to the disease control.

Animal House Conditions
Test System and Animal Husbandry
Test Species: Rats
Strain: Albino wistar
Sex: Male and Female
Age: 2 Weeks
Body Weight: 20-40 gms
Source: In house breed
CPCSEA Registration Number-1803/PO/RcBi/S/2015/CPCSEA
Animal House conditions
Lighting: 12/12 hour light-dark cycle
Temperature: 22±3° C.
Relative Humidity: 30 to 70%
Animals had continuous access to fresh, potable, uncontaminated drinking water.
Feed: Normal chow diet [Amrut Feeds, Krishna valley Agrotech LLP, Source: Prashanth Enterprises, Pune]

The study was commenced after the protocol reviewed and approved by Institutional Animal Ethical Committee (IAEC) of Radiant Research Services Pvt. Ltd

TABLE 8

Test items, Vehicle and Formulation details

| Test item | G3 (Agmatine sulphate) | G4 (Nicotinamide Riboside chloride) |
|---|---|---|
| Dose | 25.83 mg/kg | 6.46 mg/kg |
| Route | Oral | Oral |
| Frequency | Daily for 26 days. | Daily for 26 days. |
| Vehicle | 0.5% Carboxy Methyl Cellulose sodium | 0.5% Carboxy Methyl Cellulose sodium |

TABLE 9

Group, Designation and Dose Levels

| Groups | Group Description | Treatment | Dose Level | Dose Volume (ml/kg) | No. of animals |
|---|---|---|---|---|---|
| Group-1 | Normal Control | 0.5% CMC | 0.0 mg/kg (Vehicle) | 10 ml | 5M + 5F |
| Group-2 | Disease control | VPA | 400 mg/kg | 10 ml | 5M + 5F |
| Group-3 | Test 1 | Agmatine Sulphate | 25.83 mg/kg | 10 ml | 5M + 5F |
| Group-4 | Test 2 | Nicotinamide Riboside chloride | 6.46 mg/kg | 10 ml | 5M + 5F |
| Group-5 | Test 1 + Test 2 | Agmatine Sulphate + Nicotinamide Riboside chloride | 25.83 mg/kg + 6.46 mg/kg | 10 ml | 5M + 5F |

Study Procedure:

The experiment was performed in 14-day old male and female offsprings. The weight of the rat pups on the first day of the experiment was 20-40 grams. Sodium Valproate at dose of 400 mg/kg was freshly prepared and administered via subcutaneous route to the rat pups on postnatal day 14 (PND 14). All the animals were divided into five groups and each group contained the same amount of male and female offspring (5 males and 5 females, per group). Animals in Group-1 served as Normal control and were treated with 0.5% CMC, Group-2 served as Disease control and were treated with VPA (400 mg/kg) via intraperitoneally (i.p.), whereas Group-3 was treated with Test-1 Agmatine Sulphate (25.83 mg/kg), Group-4 was treated with Test-2 Nicotinamide Riboside chloride (6.46 mg/kg) and Group-5 was treated with Test-1+Test-2 Agmatine Sulphate+Nicotinamide Riboside chloride (25.83 mg/kg+6.46 mg/kg). The assigned test substances were administered once daily from PND 14 to PND 40. In addition, behaviors of experimental animals were determined via Morris water maze and open field test.

Dose Administration:

The test item formulations were administered once each day by oral route at the dose levels of 25.83 mg/kg (agmatine sulphate), 6.46 mg/kg (nicotinamide riboside chloride) and 25.83 mg/kg+6.46 mg/kg/day (agmatine sulphate+nicotinamide riboside chloride), to rats of corresponding groups for a minimum of 26 consecutive days at approximately same time each day (±1 hour). The dose volume administered to each rat was 10 ml/kg/day. Similarly, 0.5% CMC for Normal control and Disease control groups was administered orally at the same dose volume for a minimum of 26 consecutive days. The dose volume was calculated for individual animals on the first day of the treatment and was re-calculated according to the recent body weights recorded during the study. Daily individual dose volumes were recorded in the study records.

Results:

Behavioural Observation

A. Morris Water Maze Test

The animals were exposed to a pool consisting of 4 quadrants (Northeast, Southeast, Southwest, and Northwest) which was filled with tap water (25° C., 40 cm deep) and covered with nontoxic milk. The removable platform was immersed below the water surface of one quadrant. Each animal had to memorize the location of the immersed platform by using specific visual cues placed around the outside of the tank. The time spent by each rat in finding and climbing on the immersed platform was recorded as the escape latency. Twenty-four hours later, the animal was re-exposed to the same condition, except that the immersed platform had been removed. The mean time that each rat spent in the target quadrant in order to search for the missing platform was noted as the retention time and was used as the index of retrieval memory. Both the escape latency and the retention time in a 5-minute exposure time were used as indices of learning and memory. A blind observer always stood at the same position, and care was taken not to disturb the relative location of water maze with respect to other objects in the laboratory. The determination of the spatial memory capacity via this test was done on PND 40.

B. Open Field Test

All the animals were exposed to open field tests after the oral treatment with various tests, standard and control treatment in respective groups. The open field apparatus consisted of a wooden field of half square meter with a series of squares alternatively painted in black and white. It had a wall of 50 cm height and was placed in a dimly lit room. Animals were treated with vehicle and the drug and were placed in the middle of the open field. Then the number of squares visited by the animals was counted for a 6 minute session. The number of entries by respective groups was recorded and used to determine the active time duration of animal post dosing. The determination of the hyperactivity of animals via this test was done on PND 40.

TABLE 10

Effect of test substance on Rat physical parameters
Morris water maze test

| | | Male | | Female | |
|---|---|---|---|---|---|
| Group | Treatment | Escape latency | Retention time | Escape latency | Retention time |
| Group-1 | Normal control | 8.20 ± 0.66*** | 13.80 ± 0.37*** | 9.00 ± 0.32*** | 14.60 ± 0.51*** |
| Group-2 | Disease control | 22.00 ± 0.89 | 37.80 ± 0.80 | 24.40 ± 0.51 | 36.60 ± 0.51 |
| Group-3 | Test-1 | 14.00 ± 0.71*** | 24.20 ± 0.73*** | 14.20 ± 0.37*** | 24.80 ± 0.58*** |

TABLE 10-continued

Effect of test substance on Rat physical parameters
Morris water maze test

| | | Male | | Female | |
|---|---|---|---|---|---|
| Group | Treatment | Escape latency | Retention time | Escape latency | Retention time |
| Group-4 | Test-2 | 15.40 ± 0.51*** | 26.20 ± 0.49*** | 15.20 ± 0.37*** | 26.40 ± 0.68*** |
| Group-5 | Test-1 + Test-2 | 9.80 ± 0.37*** | 16.80 ± 0.37*** | 10.60 ± 0.24*** | 18.40 ± 0.40*** |

Values were expressed as mean ± SEM (n = 10), Statistical significance are compared between Disease Control (Group 2) versus other treatment groups (G1, G3, G4 & G5)
(* P Value < 0.05;
** P Value < 0.001;
***P Value < 0.0001).

TABLE 11

Effect of test substance on Rat physical parameters
Open Field Test

| | | No. of squares visited for 6 mins | |
|---|---|---|---|
| Group | Treatment | Male | Female |
| Group-1 | Normal control | 67.80 ± 0.58*** | 72.60 ± 0.81*** |
| Group-2 | Disease control | 114.00 ± 1.87 | 113.40 ± 2.04 |
| Group-3 | Test-1 | 86.20 ± 2.06*** | 85.40 ± 1.03*** |
| Group-4 | Test-2 | 88.40 ± 0.98*** | 87.20 ± 0.97*** |
| Group-5 | Test-1 + Test-2 | 73.00 ± 0.54*** | 78.60 ± 0.67*** |

Values were expressed as mean ± SEM (n = 10), Statistical significance are compared between Disease Control (Group 2) versus other treatment groups (G1, G3, G4 & G5)
(* P Value < 0.05;
** P Value < 0.001;
***P Value < 0.0001).

Discussion

Autism is a highly complex developmental disorder characterized by several behavioral impairments, including decreased social interaction and communication and repetitive/stereotyped behaviors and called "autism spectrum disorder" (ASD). The neuropeptide oxytocin (OXT) plays a critical role in regulating social behaviors in the central nervous system, as indicated in both human and animal studies. Postnatal exposures to the antiepileptic drug Valproic acid (VPA) to rat pups show profound deficits in the social domain. The altered social behavior displayed by Valproic acid exposed rats may be due to either a deficit in social reward processing or to a more general inability to properly understand and respond to social signals. This present study was to evaluate the effect of test substances in autistic like behaviors of valproic acid induced autism spectrum disorder in rat model.

During this study, no significant change in body weight and feed consumption of any group was observed compared to the disease control.

To identify the therapeutic effects of test substances in the autistic like behaviors of VPA exposed rats, the Morris water maze and open field tests were performed. Both of these behavioral observations tests were conducted at the end of the experimental period.

Figure 10:
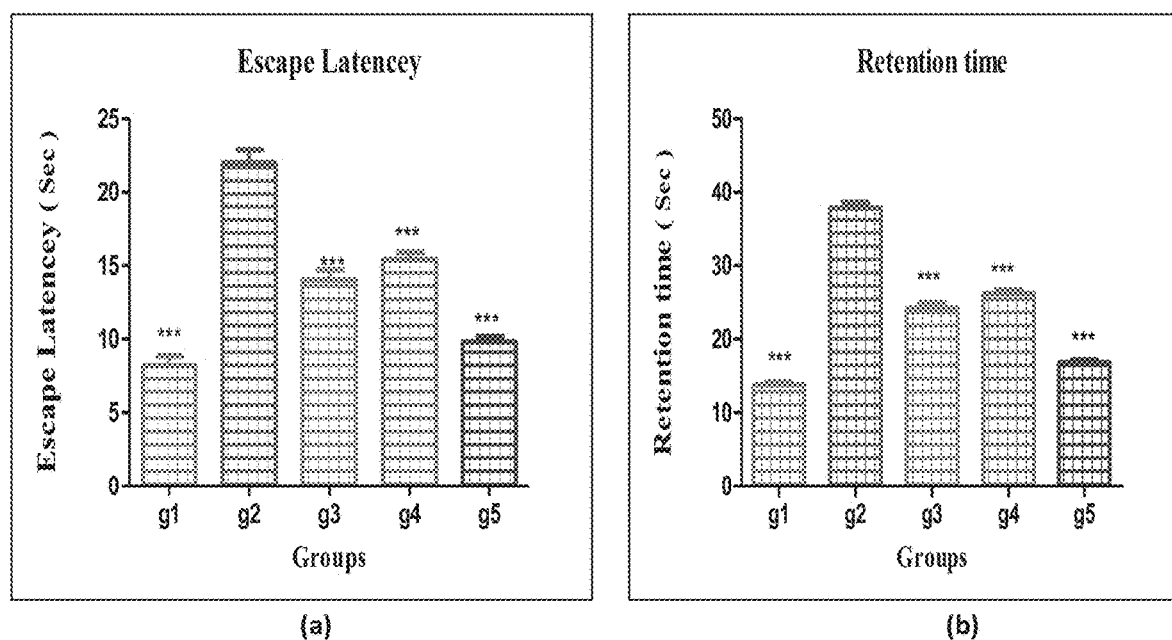
FIG. 10 illustrates the effect of test substance on Morris water maze test (a) Escape latency-male (b) Retention time—male (c) Escape latency—female (d) Retention time—female forming part of the ASD study FIG. 11 illustrate the effect of test substance on No. of squares visited in mice (a) Open field test-male (b) Open field test-female forming part of the ASD study FIG. 12 illustrate the effect of test substance on Lactate Dehydrogenase-LDH (a) LDH-male (b) LDH-female forming part of the ASD study
Figure 10:
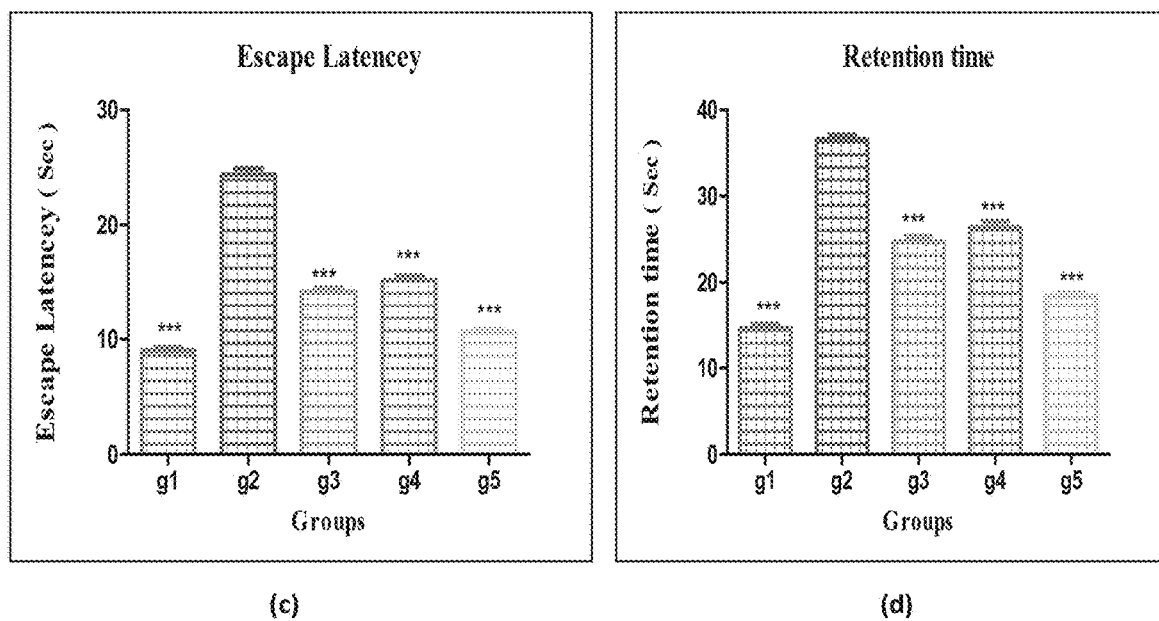

The determination of learning and memory enhancing activity of all the animals was determined by Morris water maze test on PND 40. Postnatal VPA treatment impaired learning and memory deficit behavior of all animals except control group, while test substances Group-3 (Agmatine Sulphate), Group-4 (Nicotinamide Riboside chloride) and Group-5 (Agmatine Sulphate+Nicotinamide Riboside chloride) treated groups showed significantly increased learning and memory activities compared to the Disease control. This present study concluded that the combination of test substances Agmatine Sulphate and Nicotinamide Riboside chloride (Group-5) showed better activity compared to Group-3 and Group-4 (Refer Table 10 & FIG. 10).

Figure 11:
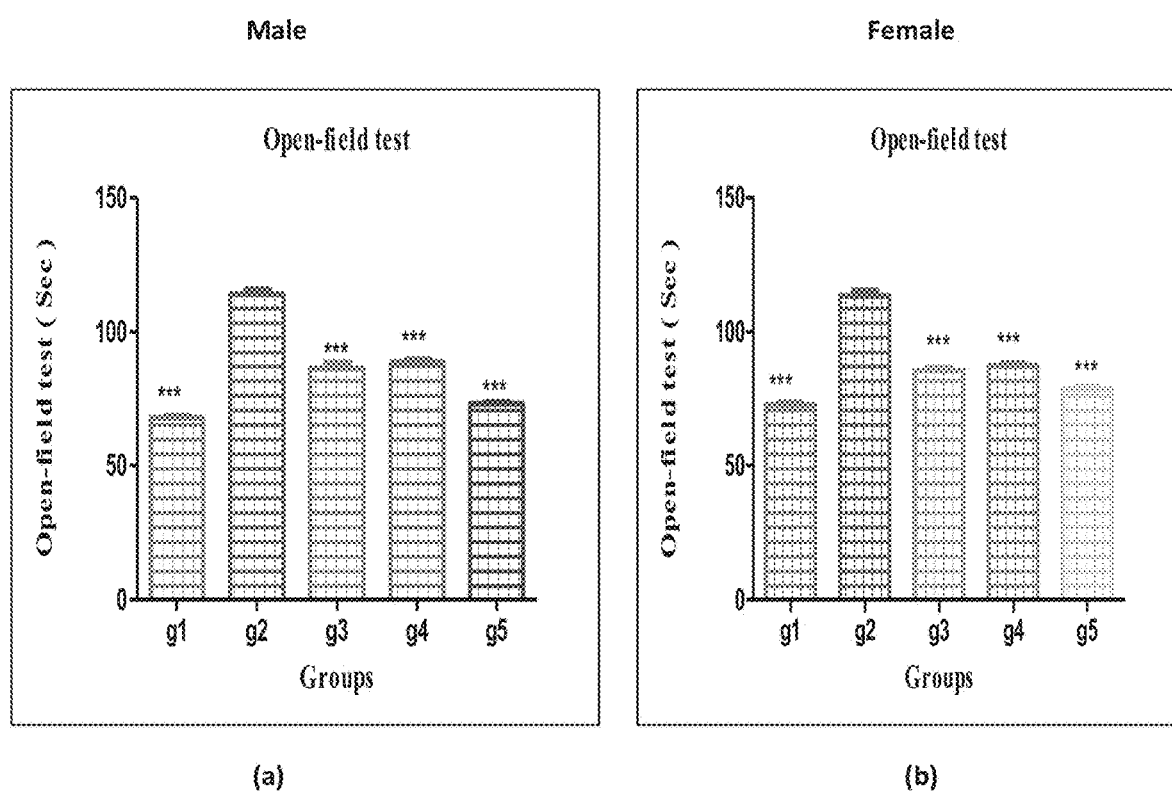

The locomotor activities of all the animals were determined by Open field test on PND 40. Postnatal VPA exposure treatment induces hyperactive behavior in all the animals except control group. The locomotor activity of animals was observed in a time period of 20 minutes. The test substances Group-3 (Agmatine Sulphate), Group-4 (Nicotinamide Riboside chloride) and Group-5 (Agmatine Sulphate+Nicotinamide Riboside chloride) treated groups exhibited significantly decreased hyperactive behavior compared to the Disease control. This study demonstrated that the combination of test substances Agmatine Sulphate and Nicotinamide Riboside chloride (Group-5) showed better activity compared to Group-3 and Group-4 (Refer Table 11 & FIG. 11).

Figure 12:
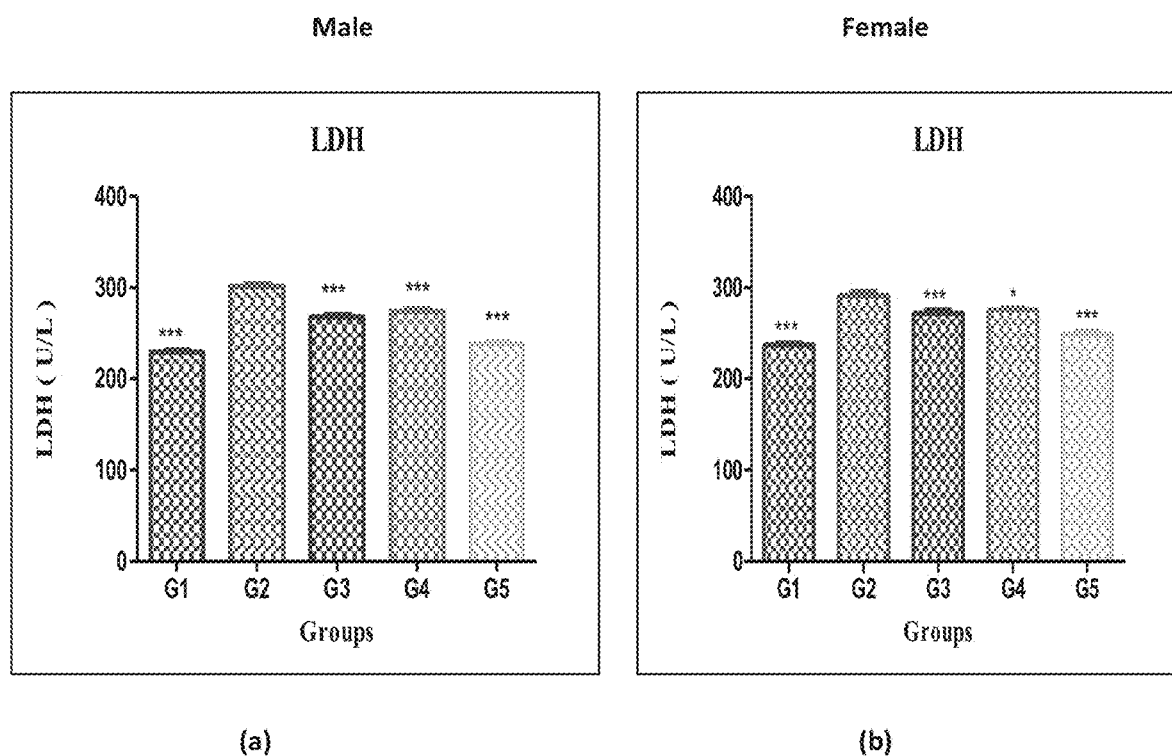

Lactate dehydrogenase (also called lactic acid dehydrogenase or LDH) is an enzyme found in almost all body tissues. It plays an important role in cellular respiration, the process by which glucose (sugar) from food is converted into usable energy for our cells. In VPA exposed rats, elevated level of Lactate dehydrogenase were seen, while test substance Group-3 (Agmatine Sulphate), Group-4 (Nicotinamide Riboside chloride) and Group-5 (Agmatine Sulphate+Nicotinamide Riboside chloride) treated groups had normalized levels of lactate dehydrogenase compared to the Disease control. This study illustrated that the combination of test substances Agmatine Sulphate and Nicotinamide Riboside chloride (Group-5) showed better activity compared to Group-3 and Group-4 (Refer Table 12 & FIG. 12).

TABLE 12

Effect of test substance on Biochemical parameters
Biochemical Parameters

| | | LDH (U/L) | |
|---|---|---|---|
| Group | Treatment | Male | Female |
| Group-1 | Normal control | 229.00 ± 2.12*** | 236.80 ± 2.08*** |
| Group-2 | Disease control | 301.60 ± 2.58 | 291.60 ± 3.78 |
| Group-3 | Test-1 | 268.20 ± 2.56*** | 272.20 ± 3.34*** |

TABLE 12-continued

Effect of test substance on Biochemical parameters
Biochemical Parameters

| | | LDH (U/L) | |
|---|---|---|---|
| Group | Treatment | Male | Female |
| Group-4 | Test-2 | 274.00 ± 3.11*** | 275.80 ± 1.71* |
| Group-5 | Test-1 + Test-2 | 237.8 ± 2.04*** | 248.8 ± 3.65*** |

Values were expressed as mean ± SEM (n = 10), Statistical significance are compared between Disease Control (Group 2) versus other treatment groups (G1, G3, G4 & G5)
(*P Value < 0.05;
** P Value < 0.001;
***P Value < 0.0001).

Conclusion

It is concluded that Group-3 (Agmatine Sulphate), Group-4 (Nicotinamide Riboside chloride) and Group-5 (Agmatine Sulphate+Nicotinamide Riboside chloride) have improved autism-like behavior in VPA model of autism disorder. Instead of the Group-3 & Group-4, Group-5 showed better behavioral activity in VPA induced autism spectrum disorder.

We claim:

1. A method comprising:
   orally administering a therapeutically effective amount of a nutritional neuroprotective composition, wherein the composition comprises an exogenous synergistic blend of agmatine sulphate and nicotinamide riboside chloride;
   reducing tumour necrosis factor (TNF) alpha levels from 172.17±6.35 pg/ml to 112.17±4.07 pg/ml, in a subject in need; and
   thereby treating depression or autism in the subject in need thereof;
   wherein the agmatine sulphate and the nicotinamide riboside chloride are present in a weight ratio of 1:0.1 to 1:1, along with pharmaceutically acceptable excipients.

2. The method according to claim 1, wherein the agmatine sulphate is present in a range of 45% to 90% by weight of the total composition.

3. The method according to claim 1, wherein the nicotinamide riboside chloride is present in a range of 10% to 45% by weight of the total composition.

4. The method according to claim 1, wherein the pharmaceutically acceptable excipients are selected from a group consisting of a diluent present in a range of 1 to 30%; a binder present in a range of 0.1 to 30%; a lubricant present in a range of 0.1 to 5.0%; a glidant present in a range of 0.1 to 5.0%; an additive present in a range of 1 to 10%; a surfactant present in a range of 0.1 to 5.0%; and a stabilizer present in a range of 0.1 to 5.0%, by weight of the total composition.

5. The method according to claim 1, wherein orally administering the composition comprises orally administering a unit dose of about 25-1000 mg of the composition.

6. The method according to claim 1, further comprising reducing interleukin-6 levels from 121.83±1.65 pg/ml to 69.56±2.24 pg/ml, in the subject in need.

7. The method according to claim 1, further comprising reducing lactate dehydrogenase levels from 301.60±2.58 U/L to 237.8±2.04 U/L in males and from 291.60±3.78 U/L to 248.8±3.65 U/L in females, in the subject in need.

* * * * *